(12) United States Patent
Crank et al.

(10) Patent No.: US 9,283,353 B2
(45) Date of Patent: Mar. 15, 2016

(54) DEVICES, SYSTEMS AND RELATED METHODS FOR DELIVERY OF FLUID TO TISSUE

(76) Inventors: Justin M. Crank, Minnetonka, MN (US); Kathryn Bertelson, Minnetonka, MN (US)

( * ) Notice: Subject to any disclaimer, the term of this patent is extended or adjusted under 35 U.S.C. 154(b) by 1276 days.

(21) Appl. No.: 13/133,119

(22) PCT Filed: Dec. 4, 2009

(86) PCT No.: PCT/US2009/006390
§ 371 (c)(1),
(2), (4) Date: Jul. 28, 2011

(87) PCT Pub. No.: WO2010/065133
PCT Pub. Date: Jun. 10, 2010

(65) Prior Publication Data
US 2011/0282318 A1  Nov. 17, 2011

Related U.S. Application Data

(60) Provisional application No. 61/140,163, filed on Dec. 23, 2008, provisional application No. 61/123,000, filed on Dec. 16, 2008, provisional application No. 61/122,784, filed on Dec. 16, 2008, provisional (Continued)

(51) Int. Cl.
*A61M 25/00* (2006.01)
*A61M 5/30* (2006.01)
*A61M 39/12* (2006.01)
(Continued)

(52) U.S. Cl.
CPC ............. *A61M 25/007* (2013.01); *A61M 25/00* (2013.01); *A61M 5/30* (2013.01); *A61M 5/3291* (2013.01); *A61M 39/12* (2013.01); *A61M 2039/1027* (2013.01)

(58) Field of Classification Search
CPC ................ A61M 5/30; A61M 5/3007; A61M 2005/341; A61M 25/0068; A61M 25/00; A61M 25/007; A61B 17/3203; A61B 2017/00247; A61B 2017/003; A61B 2017/00274
USPC ....................................................... 604/68–72
See application file for complete search history.

(56) References Cited

U.S. PATENT DOCUMENTS 4,093,108 A  6/1978  Hein et al.
4,130,119 A  12/1978  Sessions et al.
(Continued)

FOREIGN PATENT DOCUMENTS

WO  WO9616606 A1  6/1996
WO  WO9736625 A1  10/1997
(Continued)

*Primary Examiner* — Bhisma Mehta
*Assistant Examiner* — Bradley Osinski
(74) *Attorney, Agent, or Firm* — Kagan Binder, PLLC

(57) ABSTRACT

Described are devices useful to inject fluid to tissue without the use of a needle, and related methods; the devices include one or a combination of features such as ejection orifices (40), distal end control features, or combinations of these; the systems can include a fluid delivery system having an injector source and an access device; the access device can comprise a minimally invasive, tubular delivery lumen (34) such as a catheter or endoscope; the tube-like device further includes one or more apposing jets that are selectively fired to force the injection orifice of the tube-like device against the target tissue; selective firing can include a continuous firing during the injection to improve the efficiency of the treatment.

14 Claims, 20 Drawing Sheets

Related U.S. Application Data application No. 61/122,525, filed on Dec. 15, 2008, provisional application No. 61/120,204, filed on Dec. 5, 2008, provisional application No. 61/139,705, filed on Dec. 22, 2008, provisional application No. 61/122,793, filed on Dec. 16, 2008.

(51) Int. Cl.
   *A61M 39/10* (2006.01)
   *A61M 5/32* (2006.01)

(56) References Cited

U.S. PATENT DOCUMENTS

| | | | |
|---|---|---|---|
| 4,742,817 A | 5/1988 | Kawashima et al. | |
| 4,946,442 A | 8/1990 | Sanagi | |
| 5,007,897 A | 4/1991 | Kalb | |
| 5,116,313 A | 5/1992 | McGregor | |
| 5,261,889 A | 11/1993 | Laine et al. | |
| 5,336,178 A | 8/1994 | Kaplan | |
| 5,693,016 A | 12/1997 | Gumaste et al. | |
| 5,840,062 A | 11/1998 | Gumaste et al. | |
| 5,947,988 A * | 9/1999 | Smith | 606/167 |
| 6,102,886 A * | 8/2000 | Lundquist et al. | 604/22 |
| 6,203,533 B1 | 3/2001 | Ouchi | |
| 6,210,378 B1 | 4/2001 | Ouchi | |
| 6,238,336 B1 | 5/2001 | Ouchi | |
| 6,280,413 B1 | 8/2001 | Clark et al. | |
| 6,400,980 B1 | 6/2002 | Lemelson | |
| 6,537,205 B1 | 3/2003 | Smith | |
| 6,547,767 B1 | 4/2003 | Moein | |
| 6,641,553 B1 | 11/2003 | Chee et al. | |
| 6,905,475 B2 | 6/2005 | Hauschild et al. | |
| 7,594,900 B1 * | 9/2009 | Nash et al. | 604/27 |
| 7,749,156 B2 | 7/2010 | Ouchi | |
| 2003/0163111 A1 | 8/2003 | Daellenbach | |
| 2004/0030320 A1 | 2/2004 | Chee et al. | |
| 2004/0162528 A1 | 8/2004 | Horvath et al. | |
| 2005/0192530 A1 | 9/2005 | Castellano | |
| 2005/0228225 A1 | 10/2005 | Hauschild et al. | |
| 2006/0129125 A1 | 6/2006 | Copa et al. | |
| 2007/0167921 A1 | 7/2007 | Burren et al. | |
| 2007/0225554 A1 | 9/2007 | Maseda et al. | |
| 2008/0114203 A1 | 5/2008 | Crank | |
| 2008/0119784 A1 | 5/2008 | Roychowdhury | |
| 2008/0119823 A1 | 5/2008 | Crank | |
| 2009/0124974 A1 | 5/2009 | Crank et al. | |
| 2009/0312696 A1 | 12/2009 | Copa et al. | |
| 2011/0015614 A1 | 1/2011 | Rykhus, Jr. et al. | |
| 2011/0046600 A1 | 2/2011 | Crank | |

FOREIGN PATENT DOCUMENTS

| | | |
|---|---|---|
| WO | WO0040279 A1 | 7/2000 |
| WO | WO0066199 A1 | 11/2000 |
| WO | WO0136029 A1 | 5/2001 |
| WO | WO0207812 A2 | 1/2002 |
| WO | WO2004071612 A2 | 8/2004 |
| WO | WO2005094921 A1 | 10/2005 |
| WO | WO2006057604 A1 | 6/2006 |
| WO | WO2006063180 A2 | 6/2006 |
| WO | WO2006076699 A1 | 7/2006 |
| WO | WO2006084821 A2 | 8/2006 |
| WO | WO2006086719 A2 | 8/2006 |
| WO | WO2007038591 A2 | 4/2007 |
| WO | WO2007079152 A2 | 7/2007 |
| WO | WO2010065126 A2 | 6/2010 |
| WO | WO2010065127 A2 | 6/2010 |
| WO | WO2010065133 A2 | 6/2010 |
| WO | WO2010074705 A2 | 7/2010 |
| WO | WO2010077271 A2 | 7/2010 |
| WO | WO2011011423 A1 | 1/2011 |

* cited by examiner

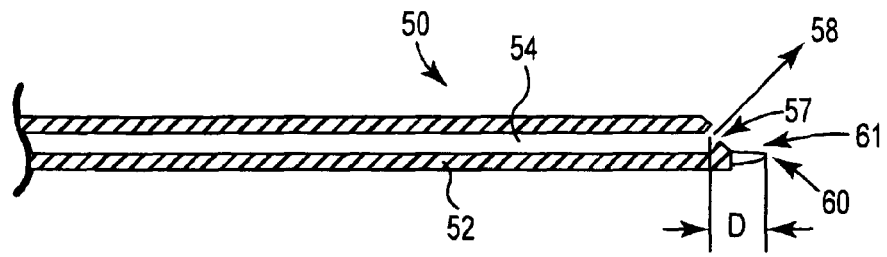
Fig. 3H
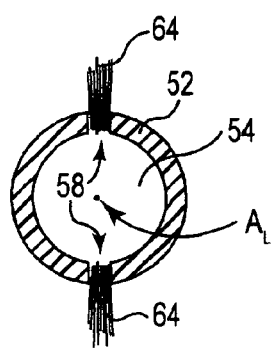 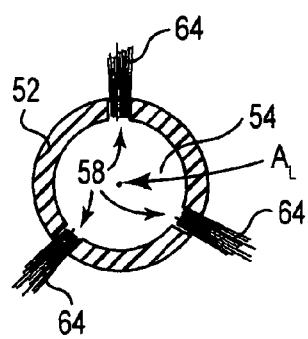
Fig. 3I  Fig. 3J
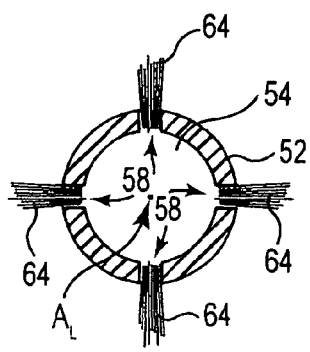 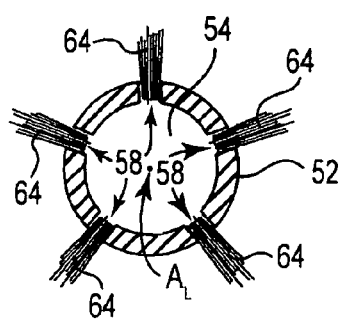
Fig. 3K  Fig. 3L

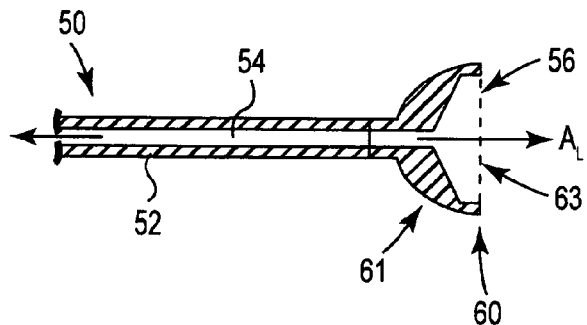 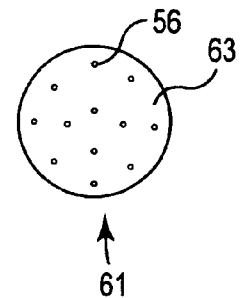
Fig. 8A  Fig. 8B
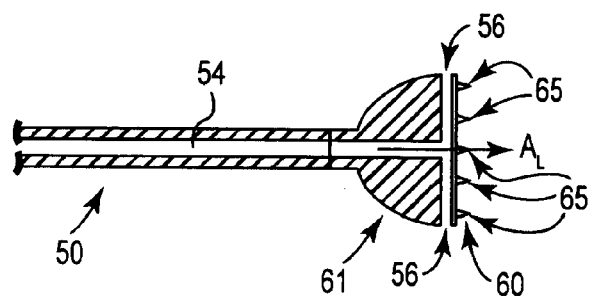 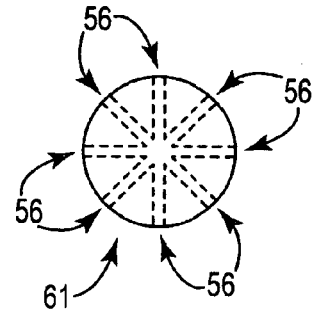
Fig. 8C  Fig. 8D
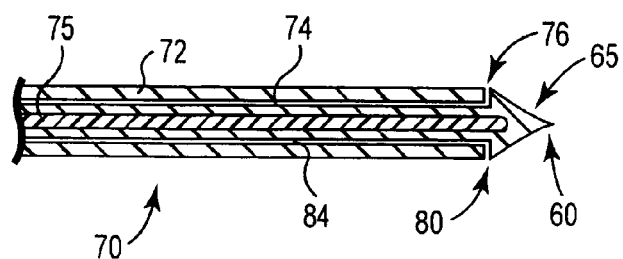
Fig. 9

DEVICES, SYSTEMS AND RELATED METHODS FOR DELIVERY OF FLUID TO TISSUE

PRIORITY CLAIM

This application claims the benefit from International Application No. PCT/US2009/006390, which was filed on Dec. 4, 2009, which in turns claims priority under 35 USC §119(e) from provisional application Ser. No. 61/140,163, filed Dec. 23, 2008, by Crank, entitled JET APPOSED JET INJECTION DEVICE; provisional application Ser. No. 61/123,000, filed Dec. 16, 2008, by Bertelson, entitled MULTI-ORIFICE SIDE-FIRING JET INJECTION BLADDER ATTACHMENT; provisional application Ser. No. 61/122,784, filed Dec. 16, 2008, by Crank, entitled JET INJECTION CATHETER TIP FOR SHALLOW INJECTIONS; provisional application Ser. No. 61/122,525, filed Dec. 15, 2008, by Crank, entitled JET-APPOSED JET INJECTION CATHETER; provisional application Ser. No. 61/120,204, filed Dec. 5, 2008, by Crank, entitled OBLIQUELY-INJECTING END EFFECTOR FOR JET INJECTION DEVICE; provisional application Ser. No. 61/139,705, filed Dec. 22, 2008, by Bertelson, entitled MULTI-ORIFICE SHOWER HEAD JET INJECTION BLADDER ATTACHMENT; and provisional application Ser. No. 61/122,793, filed Dec. 16, 2008, by Crank, entitled URINARY TRACT CATHETER WITH SHAPEABLE TIP, each of these applications being incorporated herein by reference in its entirety.

FIELD OF THE INVENTION

The present invention relates generally to needleless injection devices for the delivery of therapeutic fluids to a treatment site. Exemplary methods and devices can be used to treat tissue of the urinary tract (e.g., prostate tissue, kidneys, ureters, urethral tissue, bladder, etc.), but the methods and devices will also be useful for other treatment sites. Exemplary embodiments of devices can involve an injector body (or "shaft") having multiple orifices, one or more injection orifice as well as one or more opposing orifices for positioning the injection orifice against the target tissue, or multiple orifices for ejecting fluid in multiple directions. These and other embodiments can alternately or additionally be useful for injecting tissue at a shallow angle.

BACKGROUND

Urinary tract health is an increasingly important health issue, e.g., based on an aging population. Treatment of urinary tract conditions is an area of much investigation. Many methods and devices have been proposed to deliver therapeutic materials such as therapeutic fluid to the urinary tract, e.g., kidneys, ureters, and lower urinary tract (urethra, prostate, bladder, bladder neck).

Much effort has been focused on treating prostate tissue. Prostate disease is a significant health risk for males. Diseases of the prostate include prostatitis, benign prostatic hyperplasia (BPH, also known as benign prostatic hypertrophy), prostatic intraepithelial neoplasia (PIN), and prostatic carcinoma.

In addition to prostate conditions, other tissue of the urinary tract can be affected by medical conditions that can be treated by delivery of various therapeutic materials in the form of fluids. Tissues of the bladder (which includes the bladder neck), ureter, kidneys, urethra, as well as the prostate, can be treated by delivery of drugs or other therapeutic agents.

Various treatments of the bladder that are currently used or proposed, such as transurethral administration of an active pharmaceutical agent, involve placement of a therapeutic fluid into the bladder using a single needle located at the distal end of a rigid shaft inserted into the bladder through the urethra. These methods can involve various difficulties or undesired effects and can be difficult to perform.

Needleless devices and methods for treating tissue of the urinary tract are discussed in Applicants' copending application Ser. No. 12/087,231, filed Jun. 27, 2008, by Copa et al., titled DEVICES, SYSTEMS, AND RELATED METHODS FOR DELIVERY OF FLUID TO TISSUE, and U.S. Publication No. 2006-0129125, the entireties of these disclosures being incorporated by reference. A wide variety of medical treatments are at least partially performed through the delivery and introduction of therapeutic compositions to a treatment location by way of needless injection. For example, diseases of the prostate such as prostatitis, benign prostatic hyperplasia, and prostatic carcinoma, are treated by injection. Surgical methods used to relieve the symptoms of BPH include methods of promoting necrosis of tissue that blocks the urethra by chemical ablation (chemoablation). In one chemical ablation technique, absolute ethanol is injected transurethrally into the prostate tissue. This technique is known as transurethral ethanol ablation of the prostate (TEAP). The injected ethanol causes cells of the prostate to burst, killing the cells. The prostate shrinks as the necrosed cells are absorbed.

One way in which therapeutic fluids can be delivered internally is through the use a tube-like device configured to provide a jet-injection of the therapeutic fluid at a desired treatment site. Generally, a needleless injector is to deliver the therapeutic fluid from an external reservoir located at a proximal end of the tube-like device with such administration occurring at a distal end of the tube-like device. Due to the relatively long travel length of the therapeutic fluid through the tube-like device, the remote injector must generally be capable of pressurizing the therapeutic fluid to pressures exceeding about 2,000 psi. To accommodate these pressures, the tube-like devices have been fabricated of alloys such as NiTi or stainless steel or with metal-reinforced polymers such as the braided tubes typically found in catheters. While the use of alloys and metal reinforced polymers satisfy the operational requirements related to burst pressure and distention strength, they are generally of limited flexibility making them difficult to navigate within the tortuous paths often found in the human body such as, for example, the urogenital tract.

According to certain methods of injecting the prostate, a transuretheral flexible endoscopic probe is directed to the area of interest. Because a flexible endoscope is rotated inside bends, the injection tube will tend to uncontrollably rotate inside the channel of the endoscope because it does not have equal bending stiffness in all degrees of movement. Moreover, the articulating section of the flexible endoscope can typically only bend on one direction making compound bends impossible. This is a problem in the anatomy around the prostate. Therefore there is a need to fix the injection tube in a preselected orientation so as to enable an injection in the desired direction.

Furthermore, treatment is more efficiently performed if the injection orifice is proximate the target tissue. As the injection catheter is directed through the channel to the target tissue, whether within the endoscope or independently, it is unacceptable to simply rely on luck for proper placement. Thus there is a further need to direct the injection orifice proximate the target tissue with the minimum of moving parts and complexity due to the space constraints.

Different practical challenges exist for performing injections of other types of tissue. Some tissues, such as bladder tissues, are thin in their depth dimension (i.e., shallow), making injection a challenge. For these tissues, there is ongoing need to improve injections, such as by increasing uniform distribution of agents within the thin tissue, over a desired area of the tissue.

For any injection or injected tissue, therapeutic agents should be delivered with minimized discomfort and procedure time, and with the best possible degree of accuracy of delivery location and delivery volume, and with uniform and accurate distribution of a fluid throughout injected tissue. As such, there exists continuing need to provide improved devices for delivering therapeutic fluids to different tissues including but not limited to locations of the urinary tract including the bladder, bladder neck, prostate, urethra, kidneys, ureters, etc.

SUMMARY

The invention involves needleless fluid injection devices. These devices allow for localized delivery of therapeutic fluids that include biologically active species and agents such as chemical and biochemical agents, at desired anatomical tissue locations including but not limited to locations in the male or female urinary tract, e.g., bladder, bladder neck, kidney, ureters, urethra, prostate, etc. Exemplary devices can be designed to delivery fluid at various tissue locations, optionally also multiple different therapeutic fluids or multiple different tissue locations. The devices can be capable of delivery of precise amounts of fluid for injection at precise locations, for improved treatment based on precision and accuracy of fluid delivery.

Features of described devices and methods address certain practical problems associated with delivering (injecting) fluid to tissue. For example, injection of fluid to bladder tissue by use of a single needle at a distal end of a rigid shaft can require specialized dexterity and experience of a doctor due to the cumbersome nature of a rigid shaft, with just one needle. Devices and methods described herein overcome some of the challenges involved in using past tissue injection methods.

Embodiments of the described invention involve a fluid delivery system with an injector source and an access device. The access device can comprise a minimally invasive, tubular delivery lumen such as a catheter or endoscope. The injector source can include a non-metal, polymeric tube-like device for delivering a therapeutic fluid to a treatment site within a patient. The tube-like device can further include one or more apposing jets that can be selectively fired to force the injection orifice of the tube-like device against the target tissue. Selective firing can include a continuous firing during the injection to improve the efficiency of the treatment. It is envisioned that the apposing jets can have an independent source of jet fluid and an independent driving force such as a pressurized tank, magnetohydrodynamic power, expanding steam, gas power or similar methods of propulsion. The apposing jets can include nozzles or vanes to improve the ability of the operator to selectively fire the apposing jet for creating contact with the target tissue.

The non-metal, polymeric tube-like device can be fabricated using suitable high strength polymers including, for example, polyimide, polyetherimide available from General Electric under the trade name Ultem®, and linear aromatic polymers such as PEEK™, available from Victrex plc for transporting the treatment fluid and the apposing jet medium to the treatment area. In some embodiments, the non-metal, polymeric tube-like device can be reinforced through the inclusion of materials including nano-particles, clays and/or glass. In some presently contemplated embodiments, the non-metal, polymeric tube-like device can be reinforced with one or more polymers such as, for example, tubes braided with Kevlar or other high-strength polymers. The non-metal, polymeric tube-like device can be fabricated so as to have a burst strength exceeding at least about 2,000 psi and in some embodiments, having a burst strength within a range of about 2,000 psi to about 5,000 psi. The non-metal, polymeric tube-like device can be fabricated so as to have distention properties, wherein one or more orifices or jet ports located at a distal end of the polymeric tube-like device retains its shape and/or size without suffering swelling that can have a detrimental impact on a fluid jet used to deliver the therapeutic fluid at the treatment site.

In various embodiments, devices as described can be useful for injecting tissue at different tissue depths and in any desired direction (relative to a surface of the injected tissue), including relatively deep injection ("deep injection") of fluid into tissue of any size or depth, or for shallow injection of fluid into tissue at a depth near a tissue surface, such as if the tissue is of a limited depth. Depending on the desired injection depth, orifices can be oriented at different locations along a length of a shaft and at different directions or angles relative to the shaft.

For tissue of limited (shallow) depth, such as bladder tissue, treatment of the tissue by injection may require the injected fluid to pass only a short distance beneath the tissue surface. Previous needleless methods of injecting shallow tissue have been performed by injecting a fluid stream at large angles relative to a tissue surface, such as normal (orthogonal) to a tissue surface. Upon passage through the tissue surface, the stream might disperse. In other words, prior art injection methods may allow an injected fluid stream to become dispersed after entry of the "stream" at an angle that may be normal to the tissue surface at the location of the injection. Embodiments of presently described methods allow for shallow tissue injection, for example by injecting a fluid stream at an angle that is non-normal to a tissue surface, such as a shallow angle relative to a tissue surface.

Shallow tissue injection (e.g., at an orthogonal angle) can be difficult, especially if injecting tissue that includes a membrane at a surface that must be traversed by a fluid stream prior to the fluid stream reaching desired tissue; a fluid stream would require sufficient velocity to penetrate the membrane while not passing through the shallow tissue to exit the tissue on the opposite side of the tissue. Past methods can also be very sensitive to technique: an operator of an injection device must be aware of the amount or pressure exerted by the tip of an injection device on tissue being injected, because the amount of pressure can affect the degree of penetration of a fluid stream injected at a perpendicular angle.

According to certain methods described herein, challenges of shallow tissue injection can be overcome by injecting shallow tissue with a fluid stream directed at the tissue surface at an angle that is not normal to the surface but that is directed at the surface at a shallow angle. For example, such problems can be avoided if the injection orifice that produces the jet (fluid stream) is not aimed normal to the general boundary of targeted tissue but is aimed at an angle that is non-normal, especially a relatively shallow angle relative to the boundary, e.g., parallel to the boundary, or approximately parallel to the boundary. An injection aimed parallel to the general tissue boundary effectively lengthens or "thickens" the target tissue with respect to jet penetration: the amount of distance allowed for injection (effective depth of the tissue) increases. In certain embodiments, the fluid stream can be ejected from the orifice at a location that is below the general surface of the tissue, while not penetrating the tissue surface.

Devices useful for shallow injection can include an injection orifice at a location near an end of a shaft (e.g., a distal end tip) to inject tissue by placing the distal end in an orientation normal to tissue can sometimes be referred to as "end-fire" devices. End-fire devices can be used for shallow injection method and also for deep injection methods, depending for example on the angle between the direction of the injection orifice and the longitudinal axis of the shaft.

Certain described methods and devices can be useful for relatively "deep" injection, e.g., injection to a depth that is greater than a shallow injection. Devices designed for deep injection can include one or multiple injection orifices placed at any useful location along a length of a shaft to contact tissue for injection, and at any angle. The injection orifices can be located, for example, a distance from a distal end tip that allows the injection orifice to be oriented to inject a tissue surface as the shaft is oriented lengthwise along a surface of the tissue, e.g., so a length of shaft can contact the tissue surface, such as if the shaft the portion of a shaft that includes an injection orifice is oriented parallel to a tissue surface. These devices are sometimes referred to as "side-fire" device embodiments.

Certain devices as described can include design features that allow for improved handling, placement, control, and accuracy of injected fluid in terms of location distribution, and volume of fluid delivery. For example, multiple injection orifices can be arranged along a length or a circumference of a shaft to cause forces produced by ejection of fluid to be balanced or otherwise controlled, relative to the shaft. In some embodiments a net force on the shaft created by the ejection of fluid from multiple orifices at a shaft distal end can be zero. In other embodiments, a net force on a shaft created by the ejection of fluid from multiple orifices may create a force used to control the distal end of a device. A net force may be created by ejected fluid, for example, to place an injection orifice in apposition to tissue; i.e., a net force can cause a shaft and an injection orifice to be pressed against a tissue surface, for secure engagement between the injection orifice, shaft, and tissue surface, during an injection.

Still referring to certain exemplary embodiments (e.g., that allow for improved handling, placement, control, and accuracy of injected fluid in terms of location distribution, and volume of fluid delivery) an access device can comprise a minimally invasive, tubular delivery lumen such as a catheter or endoscope; the tube-like device can further include one or more apposing jets that are selectively fired to force the injection orifice of the tube-like device against the target tissue; selective firing can include a continuous firing during the injection to improve the efficiency of the treatment. It is envisioned that the apposing jets can have an independent source of jet fluid and an independent driving force such as a pressurized tank, magnetohydrodynamic power, expanding steam, gas power or similar methods of propulsion. The apposing jets can include nozzles or vanes to improve the ability of the operator to selectively fire the apposing jet for creating contact with the target tissue.

In one aspect the invention relates to a needleless injection device that includes a flexible shaft comprising a proximal end, a distal end, a distal end tip, and an injection lumen extending from the proximal end to the distal end. The distal end includes an injection orifice at a length-wise location of the distal end on a proximal side of the distal end tip. The injection orifice is in communication with the injection lumen. The injection orifice is directed at an angle in the range from 45 to about 100 degrees relative to a longitudinal axis of the shaft at the length-wise location of the injection orifice. The shaft is capable of ejecting a fluid stream from the injection orifice, the fluid stream being capable of being injected into tissue by penetrating a tissue surface as a fluid stream at a non-normal angle relative to the tissue surface.

In another aspect the invention relates to a needleless injection device that includes a flexible shaft comprising a proximal end, a distal end, a distal end tip, and an injection lumen extending from the proximal end to the distal end. The distal end includes an injection orifice at a length-wise location of the distal end on a proximal side of the distal end tip. The injection orifice is in communication with the injection lumen. The injection orifice is directed at an angle in the range from about 10 to about 170 degrees relative to a longitudinal axis of the shaft at the length-wise location of the injection orifice. At least one additional ejection orifice is present at the distal end. The device is capable of ejecting fluid from the injection orifice in a manner to produce an injection force on the distal end. And the device is capable of ejecting fluid from the at least one additional ejection orifice in a manner to produce an ejection force that at least partially opposes the injection force.

In another aspect the invention relates to a method of injecting tissue. The method includes: providing a needleless injection device as described herein, providing an injectate at the proximal end and in communication with the injection lumen, placing the injection orifice near a tissue surface without penetrating a tissue surface, and pressurizing the injectate to cause the injectate to be ejected from the injection orifice as a fluid stream that passes through the tissue surface and disperses as fluid particles in tissue below the tissue surface.

In another aspect the invention relates to a needleless method of injecting tissue. The method includes providing a needleless injection device comprising a flexible shaft comprising a proximal end, a distal end, a distal end tip, and an injection lumen extending from the proximal end to the distal end. The distal end includes an injection orifice at a length-wise location of the distal end on a proximal side of the distal end tip. The injection orifice is in communication with the injection lumen. The injection orifice is directed at an angle in the range from about 45 to about 100 degrees relative to a longitudinal axis of the shaft at the length-wise location of the injection orifice. The method includes positioning the distal end at a location near a tissue surface and normal to the tissue surface, without the injection orifice penetrating the tissue surface, and ejecting a fluid stream from the injection orifice such that the fluid stream penetrates the tissue surface at a non-normal angle relative to the tissue surface.

In another aspect the invention relates to a needleless method of injecting tissue. The method includes providing a needleless injection device comprising: a flexible shaft comprising a proximal end, a distal end, a distal end tip, an injection lumen extending from the proximal end to the distal end, and a control lumen extending from the proximal end to the distal end. The distal end includes an injection orifice at a length-wise location of the distal end on a proximal side of the distal end tip, the injection orifice in communication with the injection lumen, the injection orifice directed at an angle in the range from 10 to about 170 degrees relative to a longitudinal axis of the shaft at the length-wise location of the injection orifice; and a control orifice. The method includes positioning the distal end at a location near a tissue surface with the injection orifice directed toward the tissue surface without the injection orifice penetrating the tissue surface, ejecting a fluid stream from the injection orifice such that the fluid stream penetrates the tissue surface, the ejection producing an injection force on the distal end, and ejecting fluid from the orifice to produce an control force to oppose the injection force.

In another aspect the invention relates to combinations of any two or more components of a needleless injection system as described herein and selected from: a console, a connector member, an injection shaft, and a working shaft.

In another aspect, a combination can as indicated can be used by steps that include: providing a needleless injection system comprising a console and multiple injection shafts; attaching a first injection shaft to the console and ejecting a first fluid to inject a first tissue of a first patient; detaching the first injection shaft; and attaching a second injection shaft to the console and ejecting a second fluid to inject a second tissue of a second patient. The combination can also include one or more connector member (e.g., detachable pressure chamber) that can also be changed between injections.

The above summary of the various representative embodiments of the invention is not intended to describe each illustrated embodiment or every implementation of the invention. Rather, the embodiments are chosen and described so that others skilled in the art may appreciate and understand the principles and practices of the invention. The figures in the detailed description that follows more particularly exemplify these embodiments.

BRIEF DESCRIPTION OF THE DRAWINGS

All drawings are exemplary and not to scale.

FIGS. 3A, 3B, 3F, 3G, and 3H are side (3G) or side-sectional views of distal ends of embodiments of injection shafts as described.

FIGS. 3I, 3J, 3K, and 3L are cross-sectional views of distal ends of embodiments of injection shafts as described.

FIGS. 8A, 8B, 8C, and 8D illustrate side-sectional and end views of distal ends of shafts as described.

FIG. 9 illustrates a side-sectional view of a distal end of a shaft as described.

DETAILED DESCRIPTION

Figure 1:
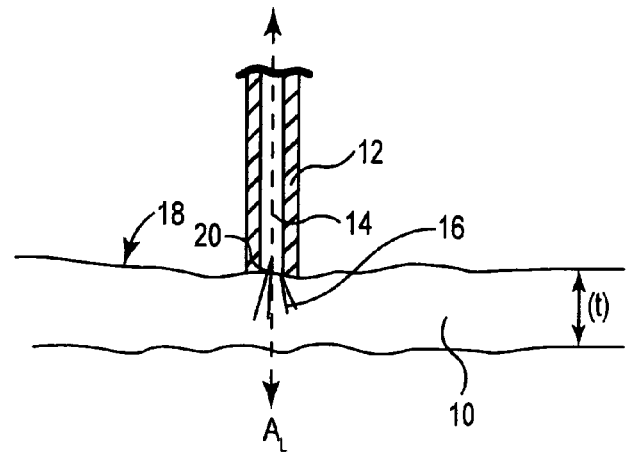
FIG. 1 illustrates a side view of a past method of injecting shallow tissue.

In the following detailed description, numerous specific details are set forth to provide a thorough understanding of various aspects of the described devices and methods. It will be apparent to those of skill in the relevant arts that described features can be practiced without these specific details. In other instances, well-known methods, procedures, and components have not been described in detail so as to not unnecessarily obscure inventive aspects.

The invention relates to devices and methods useful for injecting fluid into tissue for treatment. The fluid can be injected without the use of a needle that would include a needle structure to penetrate tissue, projecting through a tissue surface to place a needle opening within a tissue mass. A needleless injection orifice delivers fluid in the form of a stream of fluid (e.g., a "jet" or "fluid stream") at a pressure, velocity, and stream size, that allow the fluid stream to pass through a tissue surface, penetrate into the bulk of the tissue below the tissue surface, and become dispersed as fluid particles within the tissue, such as in the form of a cloud of dispersed fluid particles or droplets, without a needle structure passing into the tissue. The type of tissue injected for treatment can be any amenable tissue including but not limited to tissue at or near the urinary tract, e.g., tissue of the prostate, kidneys, ureters, urethral tissue, bladder (including the bladder neck), etc., or other tissues such as heart tissue, as desired.

Needleless devices as described generally include a distal end and a proximal end. As used herein, the "distal end" refers to a portion of the device that is located internally within a patient's body during a treatment procedure, generally including the distal end of an elongate shaft. A distal end may include functional features that operate on fluid or tissue during use, such as one or more ejection orifice, optional delivery head (end effector, nozzle, etc.) to house one or more ejection orifices, optionally a frictional tissue holding tip, optionally a tissue tensioner, optionally one or more of a light, optical feature, steering feature, etc.

A "proximal end" of an exemplary needleless device can include an injector body or "console" that remains external to the patient during use. An exemplary console can include a housing that connects to or is otherwise (directly or indirectly) in fluid communication with the shaft. The console can include fluid that can be pressurized by a pressure source to cause the fluid to flow through the shaft for injection into tissue at the distal end.

A device can eject fluid from one or multiple ejection orifices including at least one injection orifice located at the distal end of the shaft. Optionally, multiple ejection orifices may be located at one or more locations along a length of or about a circumference of a shaft distal end. An ejection orifice can be of a type designed to eject fluid to be injected into tissue, i.e., an "injection orifice." Other ejection orifices can be designed to eject fluid to produce a control force at a distal end of a shaft during an injection, i.e., a "control orifice." In some embodiments, an ejection orifice may both eject fluid for injection, and function to produce a control force, e.g., such as occurs with multiple injection orifices arranged at different locations around a circumference of a shaft at a single length-wise location. A lumen within a shaft can connect an ejection orifice (injection orifice or control orifice) at a distal end with a fluid source at a proximal end of the device; a shaft may contain one or multiple such lumens.

A shaft may include any one or more control feature to control placement of injected fluid by improving control of a distal end of a device at a location of an injection orifice. Examples of control features include the presence of multiple injection orifices directed to different tissue locations or in multiple directions around a circumference of a shaft; the use of non-injection orifices referred to as "control" orifices to offset forces produced by injected fluid; tissue tensioners; a distal end tissue holding tip that can be used to frictionally engage tissue; a steerable distal end; and combinations of these.

Devices, systems, and methods are provided that can be used to inject a fluid (sometimes referred to as an "injectate" or "injection fluid" which may be any type of fluid such as a therapeutic fluid) into tissue in a needleless manner whereby the injectate passes as a pressurized fluid stream (or "jet") through a surface of a tissue, penetrating without the use of a needle through the tissue surface and into the bulk of the tissue, and dispersing as particles or droplets within the tissue below the tissue surface. This contrasts with injections performed using a needle, whereby a hollow needle structure penetrates tissue to locate a hollow end of the needle within a tissue mass, below the tissue surface, after which the needle carries fluid into the bulk of the tissue and delivers the fluid at a relatively low pressure to the tissue in the form of a body or pool of fluid known as a bolus.

A fluid stream or jet ejected for injection into tissue by a needleless injection system can be of a size (e.g., diameter), velocity, pressure, and volume to allow the fluid stream to penetrate directly through a tissue surface, then disperse within the tissue. The stream can be considered to be a relatively high velocity, high pressure, small diameter jet that after entry through a tissue surface, disperses within the tissue, preferably as a multi-directional collection of particles (e.g., a "cloud") or droplets within the bulk of the tissue. Exemplary pressures of a fluid at a pressure chamber can be at least 200 pounds per square inch (psi), e.g., from 300 to 5000 pounds per square inch. Without limiting the scope of the present description: when injecting bladder tissue a pressure of from 250 to 1000 psi can be effective, measured at the pressure chamber; when injecting prostate tissue a pressure of from 3500 to 5000 psi can be effective, measured at the pressure chamber.

Exemplary needleless devices may be used for treating various physical ailments or conditions at any bodily tissue, for example to treat tissue that contains or is within reach of injection through a body cavity or body lumen, e.g., by accessing tissue through a body lumen, vessel, or cavity, and injecting tissue by placing an injection orifice within the lumen, vessel, or cavity. Examples of specific tissues that can be treated by injection include tissue of the urinary tract and nearby tissues, e.g., tissue of the bladder or bladder neck, kidney, ureter, urethra, prostate. Other tissues can also be treated by injection using devices and methods as described. Devices and methods as described can accommodate injection of diverse tissue types, including tissues at different locations or of different sizes, including tissues that exhibit a limited depth or thickness dimension that may be difficult to inject using other needleless (or needle-type) methods and devices. For example, certain embodiments of methods and devices can be particularly useful for injecting tissue that has a shallow "depth," by injecting the tissue laterally at a shallow angle relative to the tissue.

Exemplary devices and methods can perform shallow injection of fluid into tissue by placing an injection orifice near a tissue surface and ejecting fluid laterally to penetrate the tissue surface and become dispersed within the tissue at a location near the tissue surface. Certain tissues are somewhat shallow in depth, such as bladder tissue. Shallow injection methods may be used to treat any type of bodily tissue, if desired. Yet certain tissues, due to a shallow depth, may not be easily treated using past needleless injection methods. For example, some types of shallow tissue may be susceptible of injected fluid being passed through a shallow tissue during injection, exiting the tissue on the side opposite of the injection, possibly negating the effect of a portion of the injected fluid or placing injected fluid at an undesired location. Such tissues may not have substantial depth, e.g., are not at least 10 millimeters deep, e.g., measured between opposing tissue surfaces. Examples of tissues that can be treated using shallow injection methods as described herein include tissues that have a thickness dimension that is less than 10 millimeters, such as tissues having a thickness in the range from 2 to 10 millimeters. Such tissues include bladder tissue (including the bladder neck).

Previous needleless injection methods of shallow tissue have been performed by injecting a fluid stream at large angles relative to a tissue surface, such as substantially normal (orthogonal) to a tissue surface, or approximately orthogonal, e.g., within 10 or 20 degrees from orthogonal. FIG. 1, for example, illustrates a device and method of injecting shallow tissue, exemplary of previous methods. Referring to FIG. 1, tissue 10 has a relatively shallow thickness "t," and may be, for example, bladder tissue, which may have a thickness in the range from about 3 to 4 millimeters. Shaft 12 includes lumen 14 and orifice 20 passing through the end of shaft 12 in a direction along a longitudinal axis $A_L$ of shaft 12. Shaft 12 is oriented in an orthogonal attitude relative to tissue surface 18, at the location of contact between the end of shaft 12 and surface 18. To inject fluid 16 into tissue 10, fluid 16 is ejected from orifice 20, passes through tissue surface 18, and enters the bulk of tissue 10. Fluid 16 is injected through surface 18 and into tissue 10 by ejecting stream of fluid 16 in an orientation that is relatively orthogonal to surface 18.

In contrast, according to certain methods and devices described herein, tissue can be injected at a shallow angle relative to a tissue surface, to place injectate within a mass of tissue, near a tissue surface. The tissue may be shallow tissue such as bladder tissue. Alternately, the tissue may be non-shallow tissue such as prostate tissue or cardiac tissue, e.g., if desired to inject non-shallow tissue by placing injectate at a location near a tissue surface. Examples of shallow injection involve injecting a fluid stream into a tissue surface at a shallow angle to allow for injection and dispersal of fluid within tissue near a tissue surface, while reducing the risk that fluid passes through tissue, exiting on an opposite surface.

In many or most instances of placing a distal end tip of a shaft in contact with tissue, at a normal (i.e., orthogonal) orientation, the distal end tip will cause the tissue to deflect or deform ("indent") due to the deformable nature of soft tissue. (As used herein, a "distal end tip" can be considered a location of a distal end of a shaft that is the farthest (most distal) feature of the distal end). The size (area) of the deformed tissue will depend on factors such as the amount of pressure exerted on the tissue, the size of the distal end tip, the nature (e.g., deformability) of the tissue, among others. When injecting tissue that can become deformed or indented by pressure placed on the tissue by a distal end tip, at least a portion of the distal end of the shaft, potentially including one or more injection orifice, may become located at a position that is below a level of a surface of adjacent tissue. (See FIGS. 2A through 2D.) In these instances, the distal end tip does not necessarily penetrate the tissue surface but deforms the tissue surface so the distal end tip and optionally one or more injection orifice can become located at a position relative to nearby tissue that is "below" the tissue surface. As illustrated at FIG. 2C, for example, distal end tip 42, $D_{O2}$, and orifices 40, are located "below" line T, which intersects tissue surface 38. By this placement of a distal end tip and injection orifices, an injection orifice can access tissue laterally, and by ejecting fluid laterally can inject fluid a greater distance (i.e., a lateral distance) into the tissue.

Exemplary shallow injection methods can involve using a distal end of a shaft by orienting the distal end in an orientation that is orthogonal to a tissue surface (meaning, for example, within 20 or 10 degrees of normal, preferably within 5 degrees of normal), and placing a longitudinal (normal) force on the distal end to cause the distal end tip to exert pressure on the tissue surface. A shallow injection method can inject a fluid into tissue by injection of a fluid stream that is non-normal to the tissue surface, such as by orienting a fluid stream at an angle in the range from 0 to 45 degrees below a tissue surface, e.g., from 0 to 10 degrees, or approximately (within 10 degrees from) parallel to a tissue surface.

For purposes of measuring angles of a fluid stream relative to a tissue surface, a direction (i.e., a line) of a fluid stream can be considered to be the same direction (line) as a direction (line) defined by an axis (e.g., axis of flow) of an orifice that delivers the fluid stream. A direction (line) of a tissue surface can be a direction along a tissue surface (which surface is generally not planar, and optionally may be indented by a distal end tip of a shaft), the direction intersecting a longitudinal axis of a shaft, so the direction of the tissue surface is coplanar with the longitudinal axis, the direction of the tissue surface also being coplanar with the direction of the fluid stream. By one exemplary measurement, the direction of the tissue surface can be taken as the direction of the tissue surface at the location (point) at which the fluid stream enters tissue. See, for example, FIG. 2B and related text. By another exemplary measurement, the direction of a tissue surface can be taken as a line that extends across a distance of tissue surface, a distance away from the shaft, optionally and preferably a distance away from any tissue indented by a distal end tip of a shaft, the distance being, for example, the lateral distance to which fluid penetrates the tissue when injected at a shallow angle. See, for example, FIG. 2C and related text. A direction or line of the tissue surface can be assessed as an average location of surface tissue along a chosen distance.

Figure 2A:
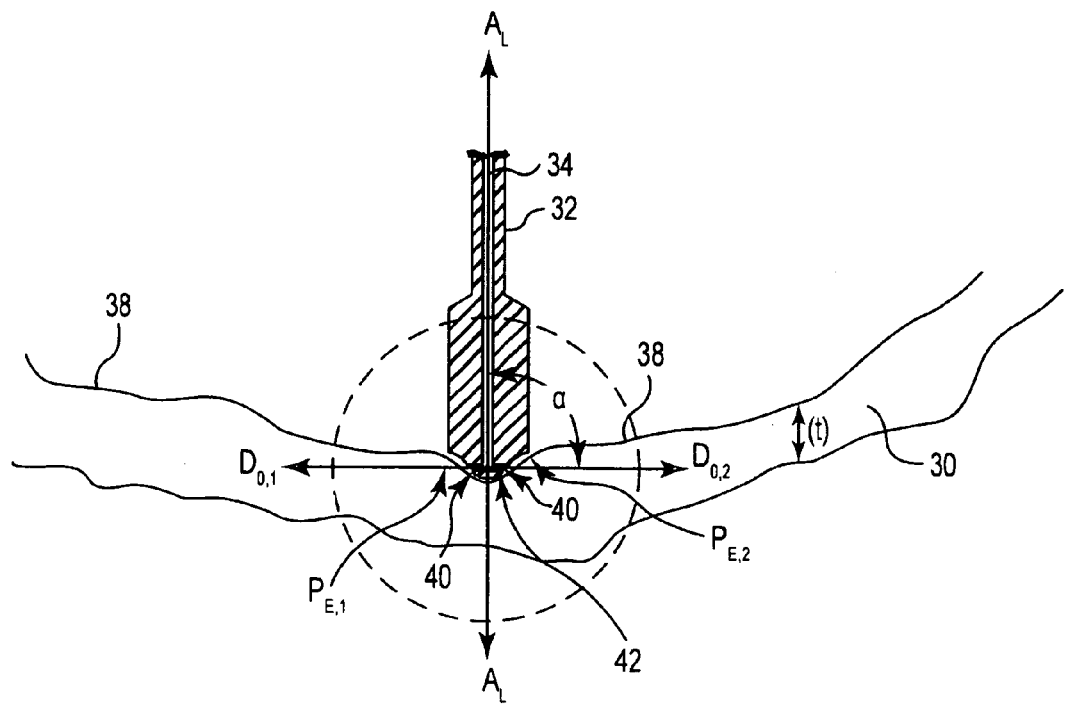
FIGS. 2A, 2B, 2C, and 2D illustrate various features and details of described methods of injecting tissue, such as shallow tissue.
Figure 2B:
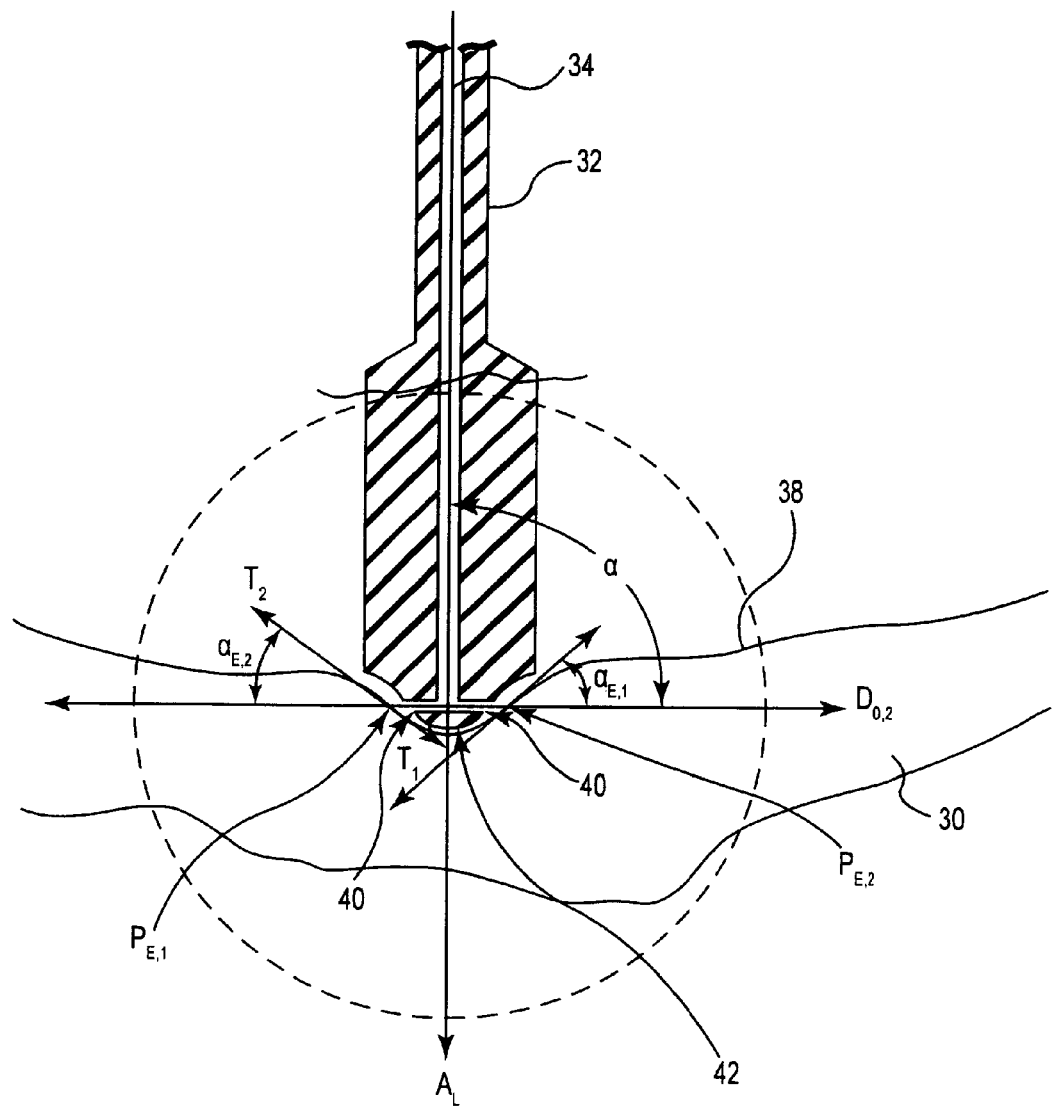
Figure 2C:
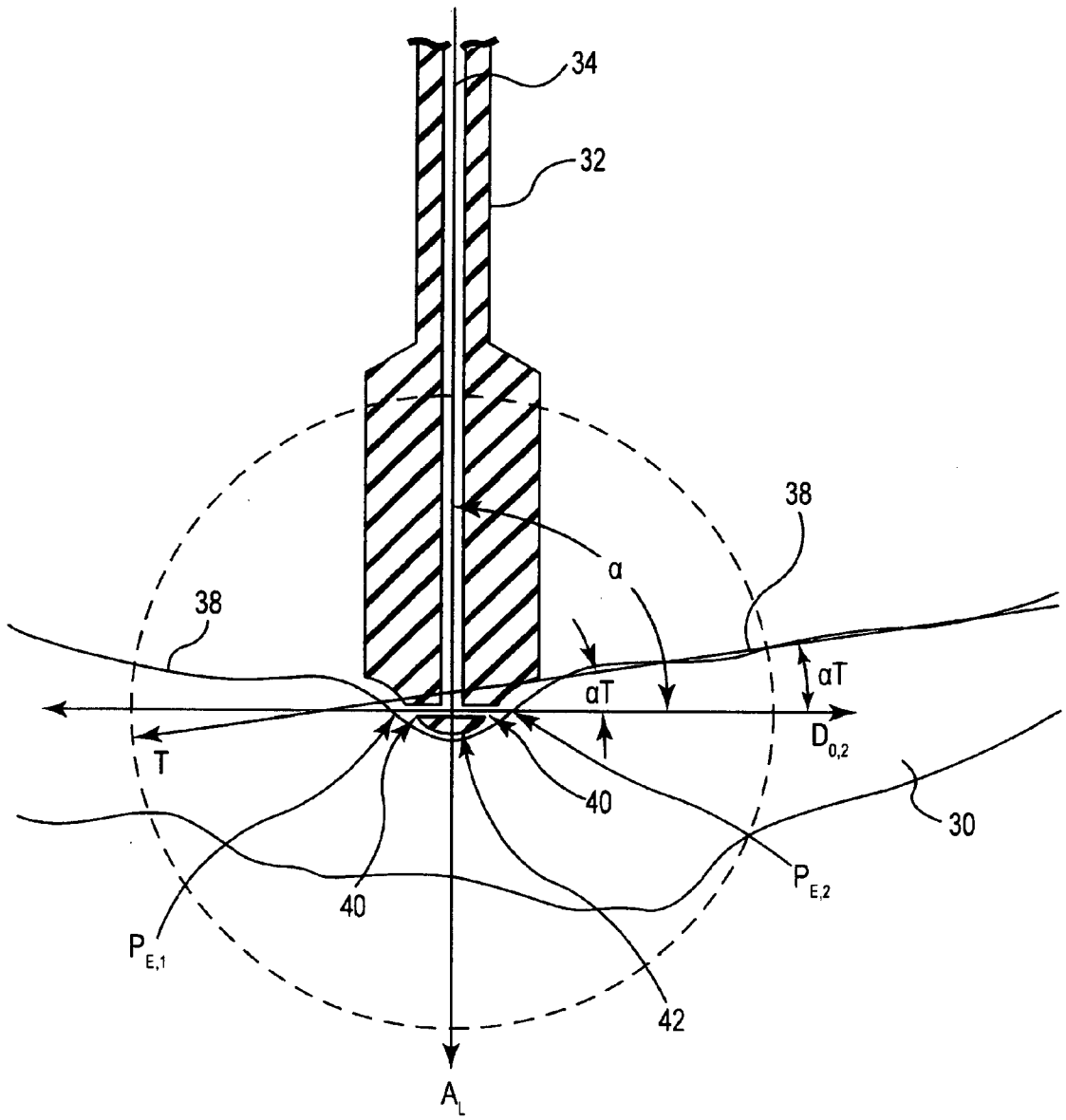
Figure 2D:
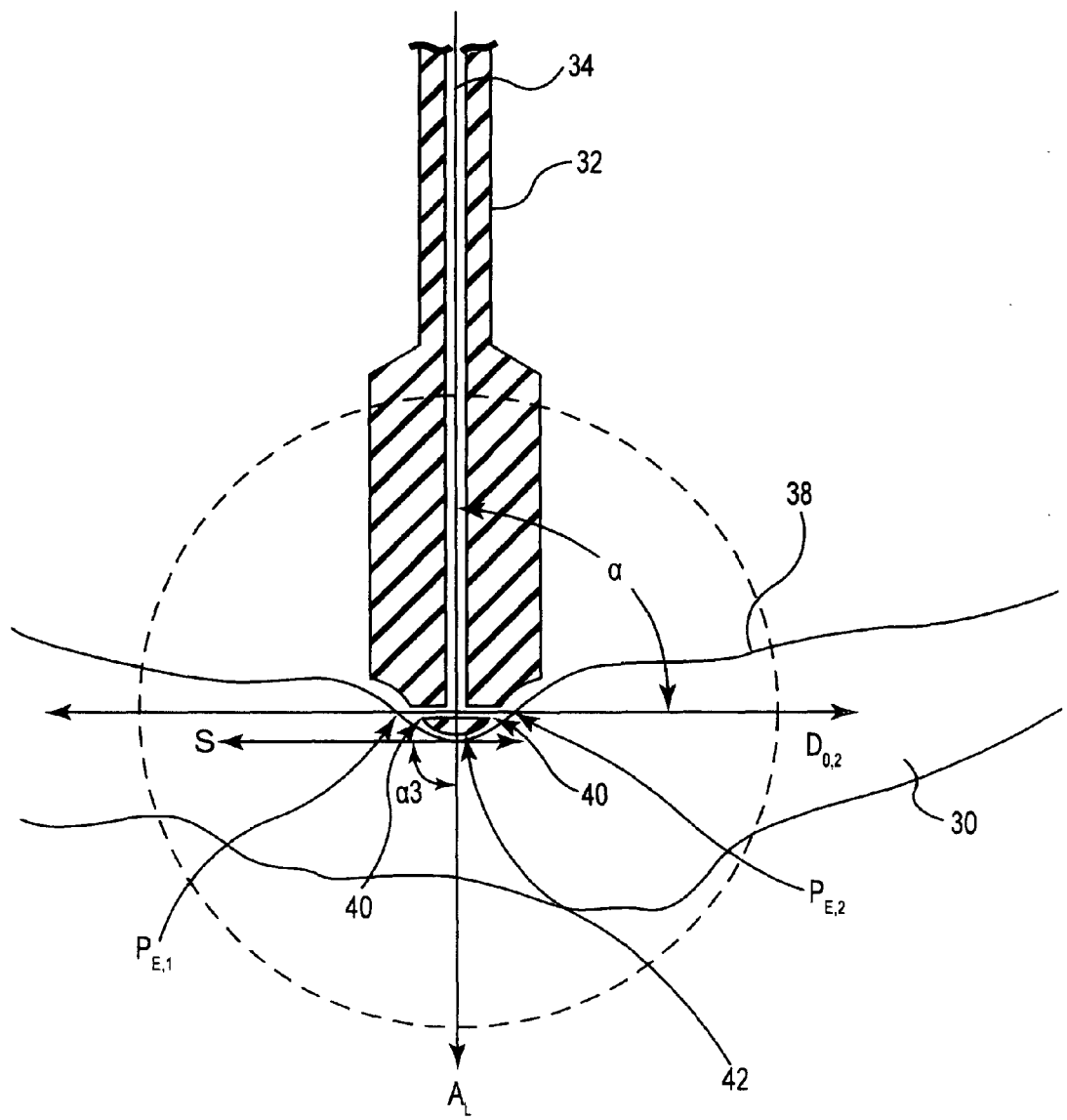

FIGS. 2A through 2D illustrate an exemplary device and exemplary method for injecting shallow tissue, at a shallow angle. (The illustrated device and method could alternately be useful to inject non-shallow tissue at a shallow angle). Referring to FIGS. 2A through 2D, tissue 30 has a relatively shallow thickness "t" and may be, for example, bladder tissue having an exemplary thickness in the range from about 3 to about 4 millimeters (mm). A portion of a distal end of shaft (e.g., injection shaft) 32 includes lumen (e.g., injection lumen) 34, two injection orifices 40, and distal end tip 42. Each injection orifice 40 is located within millimeters of distal end tip 42, and each is located at the same length-wise location along the length of shaft 32. Each orifice 40 is directed in a direction $D_{O,1}$, $D_{O,2}$, and these directions, as illustrated, are opposing directions that intersect longitudinal axis $A_L$ of shaft 32 and extend laterally at angle α, perpendicular to longitudinal axis $A_L$, which is approximately 90 degrees. Shaft 32 is oriented in a substantially orthogonal attitude relative to tissue surface 38, measured at the location of contact between distal end tip 42 and tissue surface 38 (i.e., a tangent of tissue surface 38; see FIG. 2D, showing angle $α_3$, approximately 90 degrees, between $A_L$, and tissue surface 38 (line S is tangent to surface 38 at the location at which tissue surface 38 contacts distal end tip 42).

Still referring to FIGS. 2A through 2D, fluid can be ejected from orifices 40 as a two opposing fluid streams (not shown), each of which can penetrate tissue surface 38 and become dispersed as particles or droplets within tissue 30. The fluid streams each pass through tissue surface 38 at the intersection of orifice directions $D_{O,1}$ and $D_{O,2}$, and the locations of tissue surface 38 immediately adjacent to each orifice 40. At FIG. 2B, lines $T_1$ and $T_2$ each represent a direction of tissue surfaces 38 at points of entry $P_{E,1}$ and $P_{E,2}$. As also illustrated at FIG. 2B, angles of entry $α_{E,1}$ and $α_{E,2}$ (angles between a fluid stream and a tissue surface) may generally be in the range between approximately 20 degrees and 90 degrees, depending, e.g., on the depth to which distal end tip 42 indents into tissue surface 38.

FIG. 2C illustrates an alternate embodiment of a method of injecting a fluid stream at a shallow angle between a tissue surface and an injected fluid stream (or injection orifice). As shown at FIG. 2C, line T illustrates a surface of tissue surface 38, determined as a line that intersects an average location of tissue surface 38 in a direction that intersects axis $A_L$, and that is coplanar with both $D_{O,2}$ and $A_L$. As illustrated, the angle between injection orifice 40 (as represented by line $D_{O,2}$) and an average location of tissue surface below which fluid is injected by a fluid stream ejected from injection orifice 40 (as represented by line T), may be a shallow angle, such as from about 0 degrees (i.e., an angle at which the injection stream is parallel to tissue surface T) and 45 degrees, such as from 0 degrees to about 30 degrees.

Still referring to FIGS. 2A through 2D, fluid becomes injected through surface 38 and into tissue 30 by ejecting a fluid stream from each orifice 40, in an orientation that is at a shallow angle to surface 38, as measured at points of entry ($P_{E,1}$ and $P_{E,2}$) of a fluid stream into a tissue surface. Further, as described with reference to FIG. 2C, according to these methods and devices, the fluid is also injected at a shallow angle to surface 38 as a shallow angle is measured between a direction of a fluid stream (e.g., injection orifice) and a direction of tissue below which the fluid is injected.

As will be appreciated from the present description, shallow angle tissue injection can be performed using various approaches and techniques. By certain techniques, tissue can be indented by a distal end of a shaft (e.g., by a distal end tip) to different depths, and injection orifices can be located at various positions on the distal end, e.g., on a proximal side of the "distal end tip," but near the distal end tip. A device can be designed with various and useful different shapes and geometries of a distal end, especially near a "distal end tip," such as designs that can result in indentation of tissue. Also, different orifice geometries and different orientations (angles and length-wise and circumferential positions) of one or more orifice relative to a shaft can be used, as desired. Multiple orifices may be placed around the circumference of a distal end tip, optionally in combination with a structure near a distal end tip that acts to indent or deflect tissue (e.g., a "tissue indenter") to allow an injection orifice to be located below a level of adjacent tissue. A tissue indenter can be a structure near or adjacent to a distal end tip that is designed to deflect (depress, indent, or deform) tissue to allow an injection orifice to become located at a location beneath a surface of adjacent tissue (non-indented tissue that is adjacent to the indented tissue), to allow the orifice to direct a fluid stream or jet of ejected fluid in a lateral direction to penetrate the adjacent tissue below the surface of the adjacent tissue. The injection orifice can be and aimed (directed) at a shallow angle to (e.g., parallel to) to the general boundary or surface of target tissue away from the indented tissue to allow shallow tissue injection.

Optionally, a distal end of a shaft designed for shallow tissue injection and indentation of tissue, by an end-fire design, can include a feature that provides feedback to the user as to the depth to which the distal end tip is indenting tissue, or a feature that limits the depth to which an injection orifice located near a distal end tip can indent tissue. The feedback or depth-limiting structure can be a substantially lateral extension emanating from the shaft on a proximal side of the distal end tip, also on a proximal side of the injection orifice; various examples of suitable structures include a "mane" or shoulder that extends laterally (e.g., approximately 90 degrees from a longitudinal axis of the shaft) around a circumference of the shaft, adjacent to and on a proximal side of the injection orifice, e.g., at a distance less than 5 millimeters from distal end tip; graduations as described here to visually (by an optical function of a shaft) measure a depth of indentation of a shaft distal end and an injection orifice relative to a tissue surface; or any other structural protrusion that allows feedback for a level of indentation of the distal end tip, into tissue. The depth-limiting structure may be prepared of any material suitable for a shaft or injection shaft, such as most metals, strong polymers such as PEEK, polycarbonate, Ultem™, and others. The structure and a nearby distal end tip may be of any size and geometry to allow indentation of the distal end tip and optional feedback or depth-limiting functionality, and may be formed directly from the material of the injection shaft.

A shallow injection as described can be useful to inject a fluid to a location that is a shallow distance beneath a tissue surface. This may be desirable for tissue that is of a shallow depth such as bladder tissue, or for other tissues such as heart tissue, even if the tissue is not of a shallow depth. A shallow injection may allow injection of fluid to a depth of up to about 10 millimeters below a tissue surface.

In a device useful to perform a shallow injection method, an injection orifice may be directed at an angle that is in the range from 45 degrees to about 135 degrees relative to a longitudinal axis of a shaft (e.g., an injection shaft), for example an angle that is in the range from 70 degrees to about 110 degrees from the longitudinal axis of a shaft at the location of the injection orifice. The direction (line) of the injection orifice can be measured as an axis of an injection orifice (e.g., bore or aperture) that intersects the longitudinal axis (or a tangent thereof) of the shaft, that is coplanar with the longitudinal axis (or a tangent thereof) of the shaft, and that is based on the longitudinal axis (or a tangent thereof) in a direction of the distal end tip being an angle of zero degrees and the longitudinal axis in a direction of the proximal end of a shaft being an angle of 180 degrees.

Also according to certain shallow injection methods, an injection orifice may be located at a length-wise location along a length of a distal end of a shaft, near a distal end tip, to allow the distal end to be placed normal to a surface, and to direct an ejected fluid to enter tissue at a shallow angle relative to the surface. In these embodiments an injection orifice can be located relatively near a distal end tip of a distal end of a shaft so that as the distal end of the shaft is placed normal to tissue (optionally to indent or deflect the tissue), the injection orifice is located at a location near the tissue surface and directed to inject fluid into the tissue at a shallow angle relative to the tissue surface. A useful distance between an injection orifice (measured at a center or axis of the injection orifice) and a distal end tip may be, for example, less than 5 millimeters, such as in the range between about 3 to about 1 millimeter (e.g., measured along a line that is parallel to the longitudinal axis of the shaft).

FIGS. 3A through 3D illustrate examples of distal ends of shafts that can be considered end-fire devices having one or more injection orifice located at a location to inject fluid into tissue at a shallow angle, with the shaft distal end positioned against tissue in an approximately orthogonal or normal orientation.

Figure 3A:
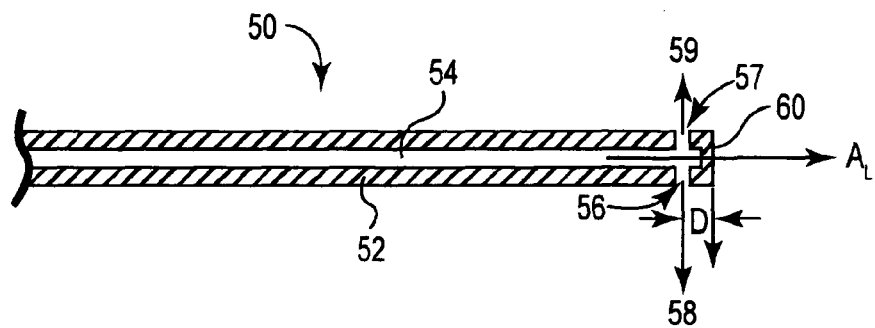

Referring to FIG. 3A, shaft distal end 50, an injection shaft, in cross-section, includes shaft sidewalls 52, injection lumen 54, and injection orifices 56 and 57, directed in opposing directions 58 and 59. Directions 58 and 59 are substantially perpendicular to longitudinal axis $A_L$. Distal end tip 60 is a surface orthogonal to longitudinal axis $A_L$. Distance D between injection orifices 56 and 57, and a plane orthogonal to distal end tip 60, can be, e.g., shorter than 5 millimeters.

Figure 3B:
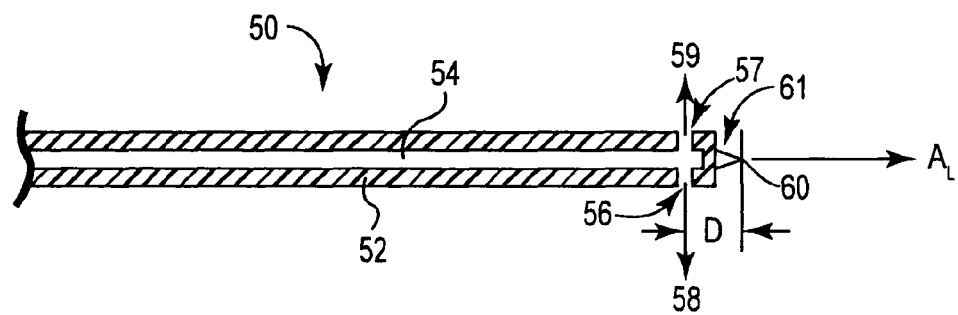

FIG. 3B shows another example of a similar shaft, this one modified to include tissue holding tip 61, adjacent to distal end tip 60 that includes a frictional extension capable of frictionally engaging tissue when distal end 50 is placed at an orientation orthogonal to a tissue surface.

Figure 3C:
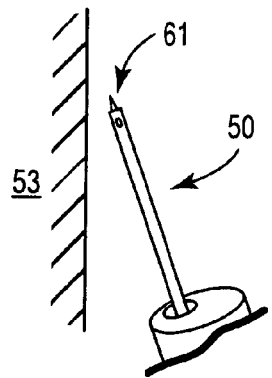
FIGS. 3C, 3D, and 3E illustrate distal ends of an embodiment of injection shaft as described, and related methods.
Figure 3D:
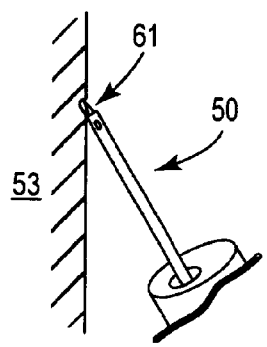

The frictional extension may be designed to frictionally engage tissue to prevent movement of distal end 50 and injection orifices 56 and 57, upon ejection of fluid from the injection orifices. Additionally or alternately, a frictional extension can be used to allow a user to place a shaft distal end at an orientation normal to a tissue surface. In some anatomical locations, a surface of a tissue may not be sufficiently accessible to allow a long injection shaft to approach a tissue surface from a normal orientation. In such instances, a shaft distal end (50) having a frictional extension or tissue holding tip 61, can approach a tissue surface (53) at a more shallow angle, e.g., from 10 to 80 degrees relative to a tissue surface, or from 20 to 70 degrees. See FIG. 3C. As shown at FIG. 3D, the tissue holding tip (61) can frictionally engage (without necessarily penetrating, but optionally merely indenting) tissue surface 53 at a non-normal angle. An operator can then manipulate flexible shaft distal end 50 using pressure and movement, e.g., by creating a curve (49) at flexible shaft distal end 50, while tissue holding tip 61 remains frictionally engaged with tissue surface 53, to place at least a portion of shaft distal end 50 near tissue surface 53, at an orientation normal to tissue surface 53. See FIG. 3E.

Figure 3E:
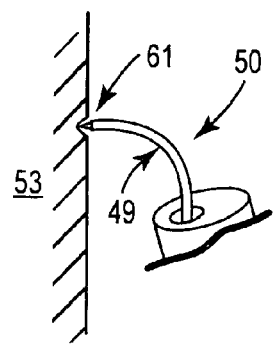
Figure 3F:
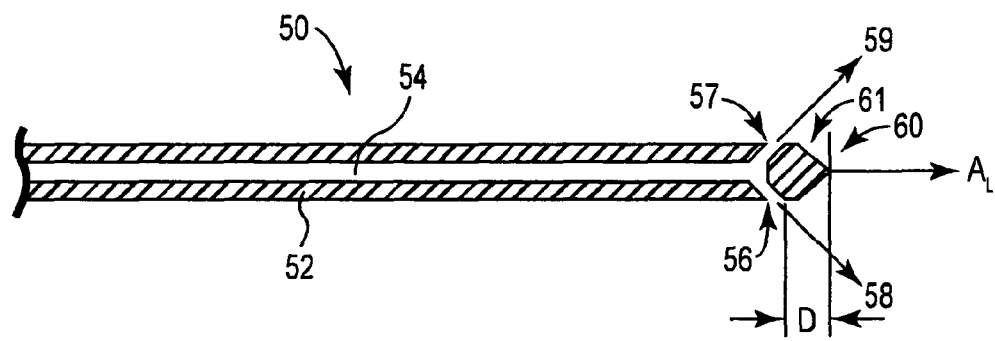

FIG. 3F shows another example of a similar shaft, this one modified to include a tissue holding tip 61, adjacent to distal end tip 60 that includes a frictional extension capable of frictionally engaging tissue when distal end 50 is placed at an orientation orthogonal to a tissue surface. Additionally, orifices 56 and 57 are directed in directions 58 and 59, respectively, angled to longitudinal axis $A_L$. The angle between directions 58 and 59 of orifices 56 and 57, and longitudinal axis $A_L$, can be, e.g., from about 60 to 30 degrees.

Figure 3G:
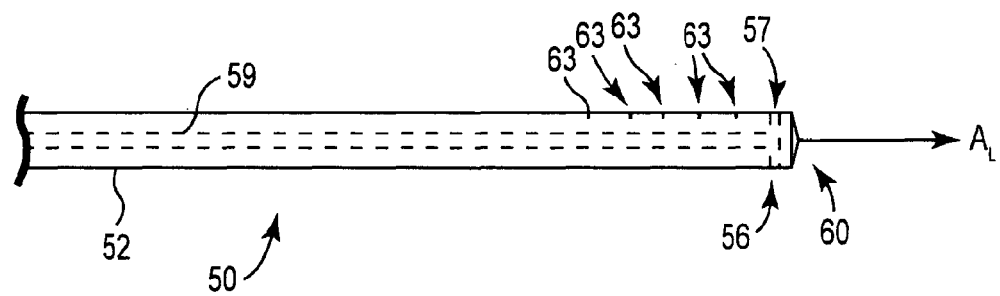

FIG. 3G (side view) shows another example of a similar shaft, this one modified to include graduations 63, which are markings on an outside surface of shaft sidewalls 52. Graduations 63 can be markings or other indications that indicate a distance from an orifice, e.g. 56, so that a degree of deflection of tissue can be measured by comparison of a tissue surface to graduations 63, using an optical feature of a working shaft. For example, a graduation can be used by placing shaft distal end 50 normal to tissue and placing normal pressure onto the shaft such that distal end tip 60 becomes located below a general tissue surface, due to indenting or deflecting of the tissue. Using an optical functionality such as that of an endoscope, cystoscope, or other working shaft or medical device shaft, the distance to which orifice 56 becomes located below a general surface of tissue, due to indentation of the tissue, can be measured according to graduations 63. Upon a desired degree of indentation, an injection can be made. Graduations 63 can be any markings, and can indicate any measure of distance, generally a small distance such as a millimeter or fraction of an inch.

FIG. 3H shows another variation of a distal end 50 that includes only a single injection orifice 58, at an angle about 45 degrees from longitudinal axis $A_L$.

Shaft distal ends 50 as illustrated at FIGS. 3A through 3H are exemplary, for example are illustrated to include one or two injection orifices. Any of these distal ends could be further modified as described herein, such as to include additional injection lumens, additional injection orifices, one or more control orifices, etc. As illustrated at FIGS. 3I, 3J, 3K, and 3L, (in cross-section at a length-wise location of multiple injection lumens along a length of the shaft) multiple injection orifices can be placed around a circumference of an injection shaft, at any desired angle or angles relative to a longitudinal axis (e.g., perpendicular to the axis, or at an angle directed distally). As shown at FIGS. 3I, 3J, 3K, and 3L, injection shaft 50 includes sidewalls 52, injection lumen 54, and injection orifices 58 (bores or apertures in sidewalls 52). Fluid streams 64 are being ejected from injection orifices 58. Advantages of multiple injection orifices at a single lengthwise location along a length of a distal end, e.g., distributed at equidistant locations around a shaft circumference, can balanced injection forces and improved uniformity of injection of tissue around the perimeter of the injection shaft. As illustrated, injection orifices are in the form of apertures or bores formed directly in shaft sidewalls; alternately, orifices can be part of a nozzle, end effector, injection head, etc.

Embodiments of the invention also allow for "deep" injection of fluid into tissue having substantial depth by placing an injection orifice near a tissue surface and ejecting fluid from the injection orifice into tissue, substantially into the tissue below the surface and not merely near a tissue surface as with shallow injection methods. Description of an injection as a "deep" injection is relative, referring to an injection that can be relatively deeper into tissue compared to a shallow injection, as discussed. Deep injection methods can be used to inject tissue to cause injectate to penetrate past a tissue surface, for example to a depth that is at least about 7 millimeters below a tissue surface, e.g., to a depth in the range from about 10 to 30 millimeters below a tissue surface. A fluid stream may be directed substantially perpendicular to a tissue surface, or at any angle.

According to exemplary deep injection methods, one or more injection orifice need not be (but at least one may be) located near a distal end tip; one or more injection orifice may be on a proximal side of a distal end tip at a location that allows the injection orifice and adjacent injection shaft sidewall to contact a tissue surface as a longitudinal axis of a shaft that contains the injection orifice is positioned in an orientation that is parallel to the tissue surface. These device embodiments are sometimes referred to as "side-fire" devices, herein.

In certain embodiments of "side-fire" devices, an injection orifice can be located a distance away from a distal end tip, on a proximal side of the distal end tip, so the injection orifice is located to contact tissue for injection by placing the shaft sidewall in contact with tissue. The injection orifice can be located at a location along a length of the distal end of a shaft a distance away from a distal end tip, so that when a sidewall of the distal end of the shaft is placed to contact tissue, such as from within a body lumen, the injection orifice is located in position to inject fluid into the tissue. Examples of injection orifice locations for these embodiments can be locations along a distal end of a shaft that are in the range from about 1 to about 40 millimeters from the distal end tip, on a proximal side of the distal end tip, e.g., such as a distance in the range from about 1 to about 25 millimeters from the distal end tip.

Examples of tissue that can be treated using a side-fire device for a deep injection method can include tissues that have a depth dimension that is at least 10 centimeters, optionally also tissue that is accessible through a body lumen or cavity. Such tissues include prostate tissue, which may be injected by passing injectate through a urethra, i.e., an injection can be initiated from an injection orifice located within a urethral lumen, the fluid stream penetrates urethra tissue, traverses the urethra tissue, and enters and penetrates prostate tissue.

A fluid stream for deep tissue injection may be directed at any angle relative to a longitudinal axis of a shaft. The angle may differ depending on the type of tissue being injected and the location of the injection orifice along a distal end of a shaft. Useful angles may generally between 5 degrees to 175 degrees relative to a longitudinal axis of a shaft (based on the longitudinal axis in a direction of the distal end tip being an angle of zero degrees and the longitudinal axis in a direction of the proximal end of a shaft being an angle of 180 degrees). Exemplary angles can include angles in the range from 20 to 160 degrees, such as angled in the range from 45 degrees to 135, or from 70 to 110 degrees.

Figure 4A:
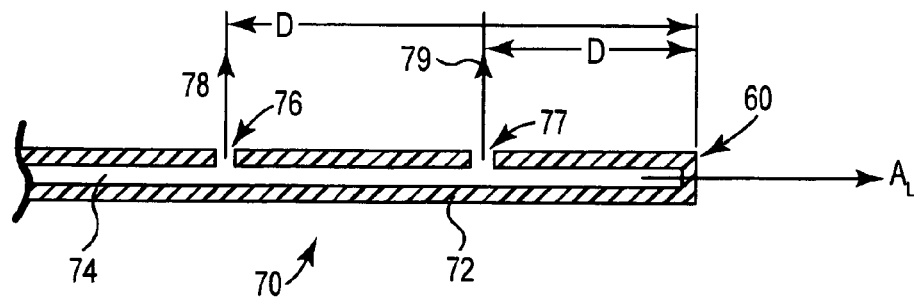
FIGS. 4A and 4B illustrate side-sectional views of distal ends of embodiments of injection shafts as described.
Figure 4B:
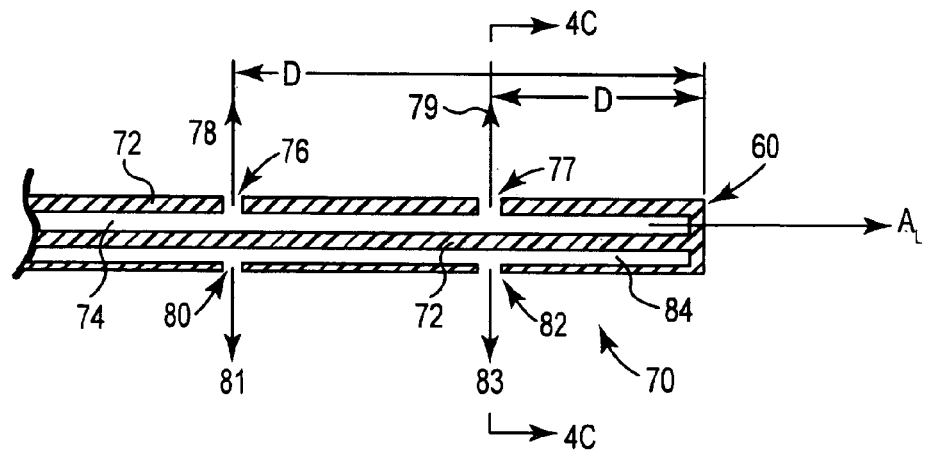
Figure 4C:
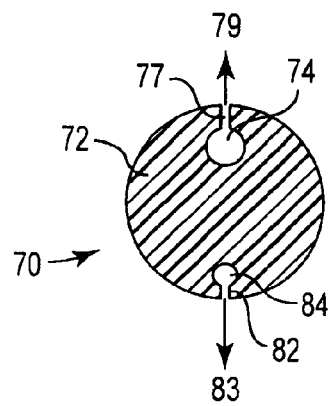
FIG. 4C is a cross-sectional view of a distal end of an embodiment of injection shaft as described.

FIGS. 4A, 4B, and 4C illustrate examples of distal ends of shaft devices that can be considered side-fire devices having one or more injection orifice located at a location along a length of the distal end of a shaft a distance away from a distal end tip, so that when a sidewall of the distal end of the shaft is placed to contact tissue, such as from within a body lumen, the injection orifice is located adjacent to a tissue surface in position to inject fluid into the tissue, through the tissue surface.

Referring to FIG. 4A, shaft distal end 70, an injection shaft, in length-wise cross-section, includes shaft sidewalls 72, injection lumen 74, injection orifices 76 and 77, directed laterally in directions 78 and 79, which are substantially perpendicular to longitudinal axis $A_L$. Distal end tip 60 is a surface orthogonal to longitudinal axis $A_L$. Distance D between injection orifices 76 and 77, and a plane that contains distal end tip 60 (i.e. orthogonal to longitudinal axis $A_L$ at the location of distal end tip 60), can be e.g., in a range between 1 and about 40 millimeters.

FIG. 4B is a variation of the shaft distal end of FIG. 4A. Shaft distal end 70 of FIG. 4B includes control orifices 80 and 82 that are directed in directions 81 and 83, opposite of directions 78 and 79. Control orifices 80 and 82 are connected to control lumen 84, which communicates with a proximal end of a needleless injection device. Control fluid can flow under pressure from the proximal end, through control lumen 84, and be ejected from each of control orifices 80 and 82. Ejection of a control fluid through each of control orifices 80 and 82, during an ejection of fluid from injection orifices 76 and 77, can produce an ejection force that opposes an injection force created by the ejection of injectate from injection orifices 76 and 77.

As illustrated at FIGS. 4A, 4B, and 4C, a single control orifice opposes each injection orifice. In alternate embodiments, more than one control orifice could be used to oppose an injection force associated with each injection orifice. Also, as illustrated, each of the two control orifices 80 and 82 is connected to the same control lumen, 84; in alternate embodiments each control orifice may be connected to a separate, different control lumen. FIG. 4C shows a cross-section end view of distal end 70 from a length-wise location at orifices 77 and 82. Also, as illustrated, injection and control orifices are in the form of apertures or bores formed directly in shaft sidewalls; alternately, orifices can be part of a nozzle, end effector, injection head, etc. Directions 78, 79, 81 and 83 are all shown to be substantially perpendicular to longitudinal axis $A_L$, but may alternately be angled relative to longitudinal axis $A_L$, such as in a direction toward distal end tip 60, or alternately, toward a proximal shaft.

According to certain embodiments of the described methods and devices, involving either deep injection methods or shallow injection methods, useful methods can involve controlling the placement of or movement of (e.g., reducing or preventing movement of) an injection orifice (and structure that supports the injection orifice such as a shaft, nozzle or nozzle head, end effector, injection shaft, or other component of a shaft located near the injection orifice) relative to tissue, during ejection of fluid from the injection orifice. Control of the placement of an injection orifice relative to tissue, and prevention of movement during an injection, can improve placement and therefore efficacy of injected fluid.

When fluid is ejected as a fluid stream from an orifice such as an injection orifice, especially at high velocity, the ejected fluid produces a force ("ejection force") on the orifice and structure supporting the orifice at a location of the ejection. The ejection force is in a direction opposite of the direction of the ejected fluid jet. (If the ejection is from an injection orifice, the ejection force can be referred to as an "injection force"). If unopposed, an ejection force (e.g., injection force) can cause movement of an ejection orifice (e.g., injection orifice) and nearby supporting structure during the ejection (e.g., injection) and, consequently, movement of the ejection orifice and structure that supports or contains the ejection orifice in the direction of the ejection force. An injection force can be sufficient to cause an injection orifice to be moved during an injection and alter or misdirect the direction of ejected fluid (injectate).

According to certain described methods and devices, an injection force can be opposed to prevent movement of an injection orifice that would be cause by an injection force produced during injection. An opposing force can be at a location that is at the same length-wise location of a shaft as an injection force, that is in the opposite direction of the injection force, and that is preferably equal to or greater in magnitude than the injection force.

According to exemplary methods, fluid can be ejected from one or more control orifice or injection orifice to produce an ejection force that opposes an injection force produced by fluid ejected from an injection orifice. An opposing force may be produced by a single orifice or a combination of two or more orifices that combine to produce a resultant force that opposes an injection force; e.g., two or more opposing forces can be used to produce a single resultant force that opposes an injection force. An opposing force from any particular ejection orifice may be less than, greater than, or equal to the injection force, to produce a combined resultant opposing force that is preferably equal to or greater than an injection force in magnitude, and in an opposite direction. In some embodiments, a resultant force that opposes an injection force may be equal in magnitude to the injection force. In other embodiments a resultant force that opposes an injection force may be greater in magnitude than and opposite in direction relative to an injection force, to result in a net force on the shaft at a length-wise location of the injection orifice that places pressure between an injection orifice and tissue to be injected.

As illustrated and described, ejection orifices can take the form of an aperture in a shaft, shaft sidewall, injection head, end effector, nozzle, or the like. Ejection orifices can be directed in any useful direction, as measured as an angle relative to a longitudinal axis of a shaft that contains the ejection orifice. Exemplary control orifices can be in the form of an aperture or bore having an axis along the direction of flow of fluid through the control orifice, and that intersects a longitudinal axis of a shaft; intersection of an axis of an ejection orifice and a longitudinal axis of a shaft can avoid forces being placed on the shaft that may tent to produce twisting or rotational movement or unbalanced pressure on the shaft.

Certain embodiments of methods and devices involve controlling, including preventing, movement of an injection orifice during ejection of a fluid from an injection orifice. Certain exemplary methods can be useful with shallow injection methods and devices that include injection orifices placed near a distal end tip, such as end-fire devices. For example, a needleless injector can involve multiple ejection orifices arranged around a circumference of a shaft, optionally each at the same length-wise location along the length of the shaft, to cause a net force on a shaft (a device shaft or a component of a device shaft such as an injection shaft, injection head, nozzle, etc.) to be balanced to produce no net force on the shaft. E.g., an injection force can be opposed or balanced by the use of multiple ejection orifices located around a circumference of a shaft. Multiple fluid streams can be ejected from the multiple ejection orifices at once, simultaneously, preferably each producing a force of equal magnitude (such as by ejecting equal flows of fluid at equal velocities), each producing a separate ejection force. Each force may be the same magnitude or different magnitudes, but the resultant force of the combined multiple ejection forces on a shaft can be balanced to prevent a net force on the shaft that would cause movement of the shaft during injection.

Referring, for example, to FIGS. 3I, 3J, 3K, and 3L, these show cross sections of shaft distal ends, at a length-wise location of a shaft, that can exhibit balanced forces produced by multiple injection orifices. In each figure, multiple fluid streams are ejected from injection orifices. Each stream is directed along a line that intersects longitudinal axis $A_L$. When all of the fluid streams ejected from multiple injection orifices of the illustrated devices produce equal injection forces, the injection forces produce a balanced force (net zero force) on the shaft.

In alternate embodiments that result in a balanced force on a shaft, one or more ejection orifices can eject a fluid that does not become injected into tissue, but that opposes (i.e., at least in part), balances, or overcomes an injection force; the fluid can be referred to as a control fluid and the orifice can be referred to as a control orifice.

Embodiments of devices and methods can involve controlling placement of an injection orifice adjacent to desired tissue by use of an ejection force in the form of a control force. During ejection of an injectate, for instance by a deep injection method, an injection orifice may desirably be placed adjacent to or against a tissue surface, e.g., in close contact with the tissue surface, to cause a jet of ejected fluid (injectate) to penetrate the tissue surface and become dispersed beneath the tissue surface, within the tissue. To improve the nature of the injection, the injection orifice may preferably be held in close contact with the tissue surface, such as with a force that causes the injection orifice (or adjacent shaft sidewall, ejection head surface, etc.) to be pressed against the tissue surface.

According to various embodiments of devices and methods, a device may include multiple ejection orifices arranged around a circumference of a shaft, optionally but not necessarily each at the same length-wise location along the length of the shaft, to cause a net force on a shaft to cause an injection orifice (or nearby shaft surface, or the like) to contact and to be placed with pressure against tissue to be injected. For example one or multiple control orifice can be directed to produce a net force ("control force") in a direction opposite of an injection force. The net ejection force from the control orifices can be in an opposite direction relative to an injection force, and of a greater magnitude than the injection force. The magnitude of the control force can be sufficiently greater than the magnitude of the injection force to cause the injection orifice to maintain contact with a surface of tissue during an injection. The control force can be applied during the injection, but also prior to the injection. Without limiting the present disclosure, generally, an force can be any amount, but may generally be no greater than about 0.5 pound-force.

Figure 5A:
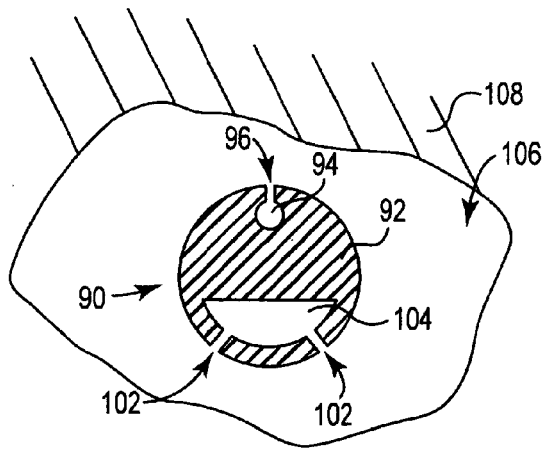
FIGS. 5A, 5B, and 5C illustrate cross sectional views of distal ends of shafts as described, and related methods.
Figure 5B:
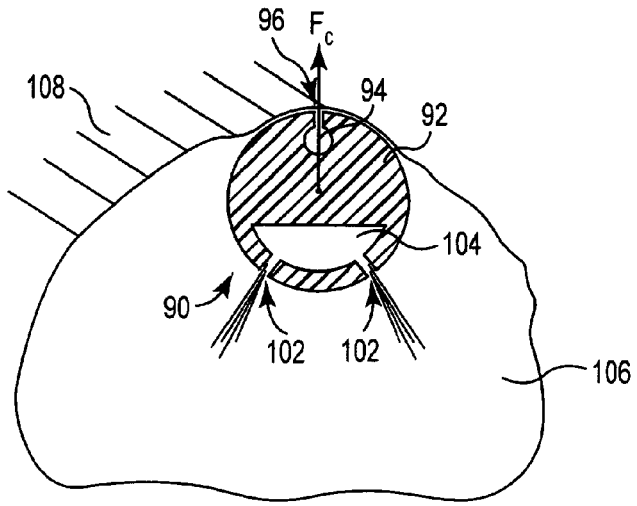
Figure 5C:
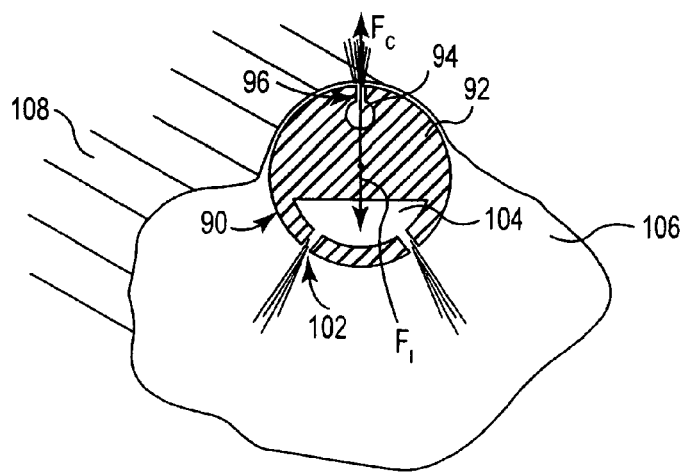

FIGS. 5A, 5B, and 5C illustrate examples (in cross-section) of distal ends of injection shafts that involve an injection force that is opposed by a control force produced by ejection of control fluid from multiple control orifices; the control orifices create an apposition force (e.g., opposing force) against an injection force, to cause apposition of the injection orifice against an injection site, to allow injection of fluid into tissue in an effective manner. Generally, methods and devices that involve control orifices for apposition (the placement of pressure of an injection orifice against tissue) during injection can involve ejection of any gaseous or liquid fluid from one or multiple control orifices, to create a control force that opposes an injection force. The control force can be opposite in direction and greater in magnitude, relative to the magnitude and direction of the injection force. A single control orifice may produce a useful control force, or multiple control orifices can be located in any desired arrangement circumferentially or axially, each producing a force, the combination of the individual forces being a resultant control force that is opposite in direction and greater in magnitude relative to the injection force. By exemplary methods, a distal end of a shaft may be placed near tissue that is to be injected; a control force may be created to cause apposition of the injection orifice, i.e., to pressure the shaft and injection orifice against tissue; with the control force in place, the injection may be performed by ejection fluid from the injection orifice placed in apposition to the tissue; after injection the control force may be removed.

Referring, for example, to FIGS. 5A through 5C, these show cross sections of shaft distal end 90, at a length-wise location of a shaft. Shaft distal end 90 includes sidewall 92, injection lumen 94, injection orifice 96, control orifices 102, and control lumen 104. Shaft distal end 90 is shown to be located within lumen 106, which may be any body lumen such as a urethra passing through a prostate.

At FIG. 5A, distal end 90 is placed within lumen 106 (e.g., a urethral lumen), which is adjacent to tissue 108 (e.g., prostate tissue). FIG. 5B shows distal end 90 within lumen 106, with control fluid (e.g., gas or liquid) being ejected from control orifices 102. A resultant control force is illustrated as vector $F_C$. Control force $F_C$ presses injection orifice 96 and adjacent sidewalls of distal end 90, against an internal surface of lumen 106. FIG. 5C shows distal end 90 within lumen 106, with control fluid (e.g., gas or liquid) being ejected from control orifices 102, and also with injection fluid being ejected from injection orifice 96. The injection force is illustrated as vector $F_I$. Control force $F_C$, which is greater in magnitude and opposite in direction relative to injection force $F_I$, continues to press injection orifice 96 and adjacent sidewalls of distal end 90, against an internal surface of lumen 106, during the injection. After the injection is completed, the control force can be removed by stopping the ejection of control fluid from control orifices 102.

As illustrated, both the injection orifices and the control orifices are in the form of apertures or bores formed directly in shaft sidewalls. Alternately, if desired, these ejection orifices can be part of a nozzle, end effector, injection head, etc. Also, FIGS. 5A through 5C show only a single length-wise location along a length of a shaft distal end, and, therefore, identify only a single set of injection orifice and control orifices; not illustrated is that the shaft distal end can optionally include one or more additional injection orifice and control orifices at other length-wise positions along the shaft distal end.

Advantages of a distal end of an injection shaft that includes control orifices for use to control the placement of the distal end, including one or more injection orifice, can be a reduced cross-sectional size, i.e., a low profile, of the distal end, compared to similar alternate distal ends that may include other mechanisms (e.g., a balloon) to position the distal end during injection. Exemplary distal ends that use control orifices may exhibit a profile that is sufficiently reduced to allow the distal end to be easily contained by a lumen of a larger shaft, such as a working lumen of a flexible endoscope, cystoscope, or catheter. The distal end may be capable of being loosely contained in a working lumen with room to be easily moved and rotated (moved longitudinally and circumferentially) within the working lumen. Additionally, a distal end of such an injection shaft can be constructed to include no moving parts, and can be of an essentially one-piece construction.

Figure 6:
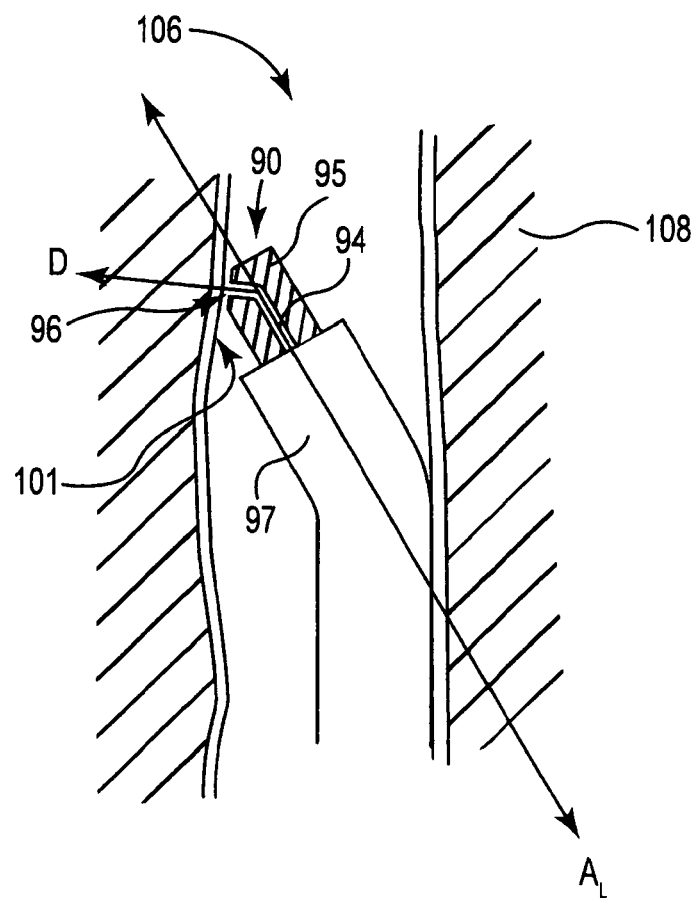
FIG. 6 illustrates a side view of a distal end of a shaft as described, and related method steps.

FIG. 6 illustrates an alternate embodiment of a device and method for deep injection of tissue, e.g., transurethral injection of prostate. At FIG. 6, distal end 90 is placed within lumen 106 (e.g., a urethral lumen), which is adjacent to tissue 108 (e.g., prostate tissue). Nozzle (or "end effector" or "injection head") 95 includes injection orifice 96 directed normal to tissue surface 101. Injection lumen 94 connects injection orifice 96 to a proximal end of a needleless injection device. Injection orifice 96 is positioned at an oblique angle, such as an angle in a range from about 45 to 70 degrees relative to longitudinal axis $A_L$ of shaft 97 and nozzle 95. Flexible shaft 97 may have flexibility, steerability, and optic features of a shaft as described herein, such as a shaft of an endoscope or cystoscope. Flexible shaft 97 allows nozzle 95 to be oriented as shown, within body lumen 97 (e.g., urethra), and, combined with injection orifice 96 being oriented at the illustrated oblique angle, a fluid stream can be ejected from orifice 96 in direction D, normal to tissue 101 within lumen 106.

According to certain embodiments of devices and methods, a distal end of a shaft, e.g., adjacent to a distal end tip, can include a structure that can mechanically hold a distal end in contact with a tissue location during an injection. In particular, for end-fire devices that place a distal end normal to a tissue surface for shallow angle injection, a frictional structure located adjacent to a distal end tip may frictionally contact and hold or grasp tissue during an injection, to oppose an injection force and prevent the distal end and the injection orifice from moving in response to an injection force. A useful engagement between a frictional tissue holding tip, and tissue, can be sufficient to engage tissue and oppose an injection force, also optionally to allow a flexible distal end to bond to a position or portion of a distal end in an orthogonal orientation relative to a tissue surface, as illustrated at FIGS. 3C, 3D, and 3E. The structure required for sufficient engagement may vary depending on factors such as the magnitude of the injection force, the amount of normal force that can be applied to the shaft distal end and between a distal end tip and a tissue surface, and the nature of the tissue. Certain types of tissue, such as bladder tissue, may be deformable, low friction (e.g., slick or slippery), or both of these. A tissue holding tip may include a frictional surface that can create a frictional force between the tissue holding tip and adjacent tissue, even slick deformable tissue, to prevent movement of the tip relative to the tissue surface, during an injection, or to allow placement of a shaft distal end at a normal orientation relative to a tissue surface by the tissue holding tip engaging tissue at a non-normal angle, followed by bending of the distal shaft end.

Embodiments of useful tissue holding tips may include one or more projections that are pointed, either to a dull or a relatively sharp point, as desired. The projections may be in the form of a dome, a spike, a cleat, a pyramid, a cone, etc., and may be sufficiently pointed (sharp) to slightly penetrate through the tissue surface, or alternately may be not sufficiently sharp to penetrate into tissue but to instead merely deflect or indent tissue.

A tissue holding tip may include a single extension that may include a longitudinal axis that is shared with a longitudinal axis of a shaft. Alternately, a single or multiple extensions may each have a longitudinal axis parallel to but offset from a longitudinal axis of a shaft. Or, a single or multiple extensions may each have a longitudinal axis that is angled from, and may or may not intercept, a longitudinal axis of a shaft. An extension can be curved or straight or bent at an angle, as desired, such as curved or bent toward or away from a longitudinal axis of a shaft.

Figure 7A:
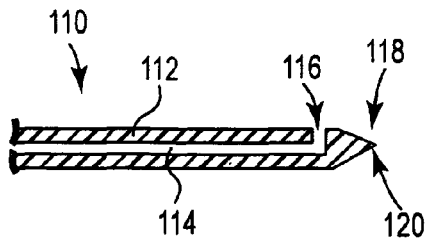
FIGS. 7A, 7B, 7C, 7D, 7E, and 7F illustrate side-sectional views of distal ends of shafts as described.
Figure 7B:
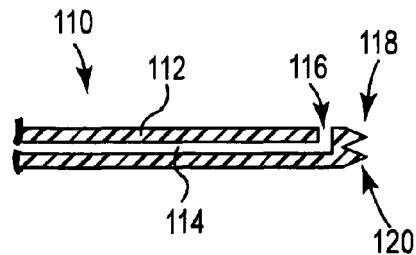
Figure 7C:
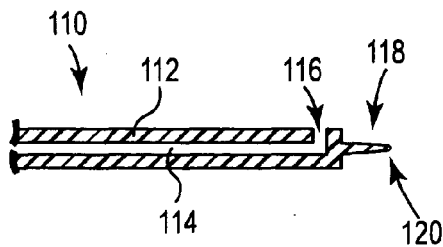
Figure 7D:
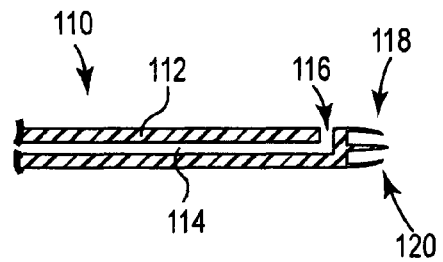
Figure 7E:
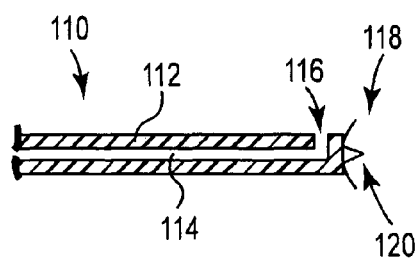
Figure 7F:
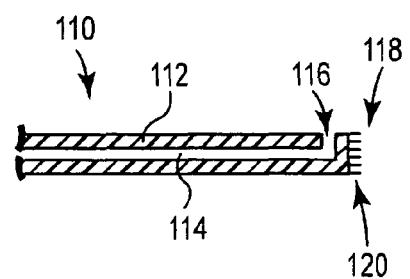

Examples of tissue holding tips are illustrated at FIGS. 7A through 7F. In these figures, shown in length-wise cross-section, distal ends 110 (of injection shafts) include sidewalls 112, injection lumens 114, injection orifices 116, tissue holding tips 118, and distal end tips 120. As illustrated, a tissue holding tip may be a single conical or pyramidal point (FIG. 7A); multiple (two or more) conical or pyramidal points (FIG. 7B); a single, straight, elongate spike having a longitudinal axis along the longitudinal axis of the shaft (FIG. 7C); multiple elongate spikes parallel with a longitudinal axis of the shaft, optionally curved at their tips (inward (as illustrated) or outward relative to a longitudinal axis of the shaft) (FIG. 7D); multiple (3, 4, 5, or more) short spines located around a perimeter of a shaft and angled away from a longitudinal axis of a shaft (FIG. 7E); and multiple (e.g., 5, 10, or more) short pyramidal or conical points, or elongate spikes, with axes parallel to a longitudinal axis of the shaft (FIG. 7F).

Exemplary needleless fluid delivery devices or systems can include a proximal end that includes a console, and an elongate shaft extending from a proximal end in communication with the console, to a distal end. One or more injection orifice at the distal end can be in fluid communication with the console.

A console generally can include a housing, a pressure chamber, and a pressure source. A console can be of any configuration, size, or design, ranging from a small, hand-held design to a relatively larger floor or table-mounted console. Optionally a console can include separate or separable components such as a pressure chamber that can be attached, used for an injection procedure, and detached and optionally discarded. A shaft can also be attached to a console or a pressure chamber in a manner to allow separation and optional re-attachment or disposal. With separable components, a shaft or pressure chamber can be attached to a console housing and used to inject a first patient or a first injectate; the shaft or pressure chamber can then be discarded or sterilized. A second shaft or pressure chamber can be attached to the console to treat a second patient or the first patient with second injectate or another amount of the first injectate. The second patient or injectate can involve injection and treatment of the same type of tissue as the first patient or injectate, or of a new type of tissue (e.g., prostate or bladder). In this manner, separable and optionally disposable shaft or pressure chamber components of a needleless injection system can allow a console housing to be used multiple times to inject the same or different injectates, to the same or different patients, and to the same or different types of body tissue.

A console can include actuating features to control distal end features, e.g., for steering a steerable distal end of a steerable shaft, to actuate ejection of fluid (control fluid or injection fluid), to move a moveable or extendable injection shaft or one or more injection orifice or control orifice relative to another shaft component such as a working shaft, optional ports to connect a console housing to auxiliary devices, electronics such as controls, and optic features such as a lens, fiber optic, or electronic viewing mechanism to allow viewing through an optical feature (to view a location of delivery). One or more attachment ports can optionally attach a console to an external and optionally remote component such as an external or remote pressure source, vacuum source, or an external or remote fluid reservoir to supply injectate or control fluid. For example, a console housing may have a fluid port that attaches to a source of a fluid (injectate or control fluid), to supply the fluid to the console housing, such as to a permanent or detachable pressure chamber. The console can include a removable or permanent pressure chamber and a pressure source capable of pressurizing a fluid contained in the pressure chamber to cause the fluid to flow from the console, through a lumen in the shaft, and then through an ejection orifice as either injectate or a control fluid.

In embodiments of devices that involve the use of a control fluid, a pressurized control fluid can be produced by a console using any useful technique and mechanism, e.g., pressure source, such as any pressurized fluid source, magnetohydrodynamic power, expanding steam or gas power, etc., with any available and useful control fluid, which may be a liquid or a gas.

Examples of consoles, console features and combinations of console features that can be useful according to the present description are identified at U.S. Pat. Publ. No. 2006-0129125 and U.S. Ser. No. 12/087,231, filed Jun. 27, 2008, by Copa et al., entitled DEVICES, SYSTEMS, AND RELATED METHODS FOR DELIVERY OF FLUID TO TISSUE, and in Assignee's copending patent applications NEEDLESS INJECTION DEVICE COMPONENTS, SYSTEMS, AND METHODS, filed on Dec. 4, 2009, by Crank, International Application No. PCT/US09/06384; METHOD AND APPARATUS FOR COMPENSATING FOR INJECTION MEDIA VISCOSITY IN A PRESSURIZED DRUG INJECTION SYSTEM, filed on Dec. 4, 2009, by Crank, International Application No. PCT/US09/06383; DEVICES, SYSTEMS AND METHODS FOR DELIVERING FLUID TO TISSUE, filed on Dec. 4, 2009, by Rykhus, International Application No. PCT/US09/06831; and METHOD AND APPARATUS FOR COMPENSATING FOR INJECTION MEDIA VISCOSITY IN A PRESSURIZED DRUG INJECTION SYSTEM, filed on Dec. 4, 2009, by Crank et al., International Application No. PCT/US09/06382, the entireties of these patent documents being incorporated herein by reference.

A fluid chamber can be a space (volume) at a proximal end of a device such as at a console housing, useful to contain pressurized or non-pressurized fluid, such as control fluid or injectate. Examples of specific types of fluid chambers include fluid reservoirs and pressure chambers. Optionally a proximal end of a device may include one or multiple fluid reservoirs and pressure chambers, optionally for one or more different fluids including one or more injectate, one or more control fluid, or combinations of these.

A fluid reservoir is generally a type of fluid chamber that can contain a fluid for a purpose of containing, transferring, holding, or storing a fluid, such as a fixed volume fluid chamber, and may be included as a permanent or removable (attachable and detachable) component of a console.

A pressure chamber can be a type of fluid chamber for containing fluid (e.g., control fluid or injectate) for a purpose of placing the fluid under pressure to deliver the fluid through a lumen to a distal end of a shaft for ejection from an ejection orifice. Examples of pressure chambers include a syringe chamber and other variable volume spaces that can be used to contain and pressurize a fluid. Examples of variable volume pressure chambers include spaces that can exhibit a variable volume based, e.g., on a plunger, piston, bellows, or other mechanism for increasing or decreasing the volume (and correspondingly decreasing or increasing pressure) within the variable volume chamber space. A pressure chamber can be pressurized by a pressure source attached to the plunger, bellows, or piston, etc., such that fluid contained in the pressure chamber is ejected under pressure, e.g., for priming a device, or for ejecting fluid from an ejection orifice for injection or to produce a control force. A pressure source may be any source of energy (e.g., mechanical, electrical, hydraulically derived, pneumatically derived, etc.) such as a spring, solenoid, compressed air, manual syringe, electric power, hydraulic, pneumatic pressure sources, etc. A pressure chamber may be a permanent or removable (attachable and detachable) component of a console or console housing.

In communication with a proximal end of a device is an elongate shaft that extends from the proximal end (i.e., from a proximal shaft end), that is optionally removably connected to the console (or a component of the console such as a removable pressure chamber), to a distal end that can be placed in a patient during an injection procedure. A shaft can be of various designs, minimally including an injection lumen to carry injectate from a proximal end of the device to a distal end of the shaft. A useful shaft may optionally include at least one separate lumen for carrying control fluid ("control fluid lumen") to a distal end.

An injection shaft minimally includes an injection lumen in communication with an injection orifice. The injection shaft can include structure such as sidewalls that define the injection lumen, the sidewalls being of sufficient strength to withstand operating pressures sufficient to deliver injectate from the injection orifice at an elevated pressure sufficient to cause the injectate to be ejected from the injection orifice to penetrate a tissue surface and become injected and into and dispersed below the tissue surface, as described herein. Exemplary elevated pressures ("injection pressures") may be 200 pounds per square inch or greater, e.g., as measured at the distal end of the injection lumen, at the pressure chamber. The pressure that will be required for any particular treatment can depend on factors such as the type of tissue being injected, the volume of injectate, etc. An injection shaft may be of a flexible material (e.g., a metal or polymeric tube) that can withstand such injection pressure, and may be prepared from exemplary materials capable of withstanding pressure of an injection, e.g., nitinol, stainless steel, reinforced (e.g., braided) polymer, as also described elsewhere herein.

A basic version of a useful shaft of a device as described can be an "injection shaft" that includes a proximal end, a distal and, a sidewall that defines an internal lumen ("injection lumen"), and at least one injection orifice at the distal end in connection with the injection lumen. An injection shaft can optionally include multiple injection orifices, optionally one or more control orifice at the distal end, and optionally a control lumen extending from the proximal end to the optional control orifice.

An injection shaft can be any elongate structure capable of delivering fluid to a distal end of a shaft at a pressure suitable to inject tissue, as described. Exemplary injection shaft structures include relatively flexible hollow bodies having a distal end, a proximal end, sidewalls extending between the ends, an internal lumen defined by interior surfaces of the sidewall. The injection lumen is in communication with one or more injection orifice at the distal end; the injection orifice may be as described herein, such as an aperture or bore in an injection shaft sidewall, an aperture or bore in a nozzle, end effector, injection head, or other structure in communication with the injection lumen.

An exemplary injection shaft can be in the form of a non-metal, polymeric tube-like device and can be fabricated using suitable high strength polymers including, for example, polyimide, polyetherimide available from General Electric under the trade name Ultem® and linear aromatic polymers such as PEEK™ available from Victrex plc for transporting the treatment fluid and the apposing jet medium to the treatment area. In some embodiments, the non-metal, polymeric tube-like device can be reinforced through the inclusion of materials including nano-particles, clays and/or glass. In some presently contemplated embodiments, the non-metal, polymeric tube-like device can be reinforced with one or more polymers such as, for example, tubes braided with Kevlar or other high-strength polymers. The non-metal, polymeric tube-like device can be fabricated so as to have a burst strength exceeding at least about 200 psi, such as at least 1,000 psi, or 2,000 psi, and in some embodiments, having a burst strength within a range of about 2,000 psi to about 5,000 psi (depending in the treatment application, and, e.g., the type of tissue being injected). The non-metal, polymeric tube-like device can be fabricated so as to have distention properties, wherein one or more orifices or jet ports located at a distal end of the polymeric tube-like device retains its shape and/or size without suffering swelling that can have a detrimental impact on a fluid jet used to deliver the therapeutic fluid at the treatment site. See, e.g., U.S. Pat. Publ. No. 2008/0119823

An exemplary injection shaft can include a sidewall that defines an outer shaft surface and an inner injector lumen, these being of continuous and relatively uniform dimensions of inner diameter, outer diameter, and wall thickness, along an entire length of the injection shaft. Alternately, an injection shaft, injector lumen, or sidewall, may change dimensions (e.g., wall thickness) along the length of the injection shaft, with a larger wall thickness (e.g., greater outer diameter) at a proximal end and a thinner wall thickness (e.g., reduced outer diameter) at the distal end. An example of an inner diameter of an injection shaft (i.e., a diameter of an injection lumen) can be greater than 0.020 inches, e.g., from 0.022 to 0.030 inches (for a lumen made of polyetheretherketone, or "PEEK"); exemplary outer diameters for the same exemplary injection shaft may be at least 0.032 inches e.g., from 0.034 to 0.045 inches. A length of an injection shaft can be any length that functions to place a proximal end at a console and a distal end at a desired tissue location; exemplary lengths can be from as little as 15 inches if the console is a hand-held console, to as long as 100 inches if the console is floor based or table based.

An injection shaft can be an only component of a shaft of a useful needleless injection device or system or may be a component of a larger shaft structure. Other shaft components may include additional elongate shaft structures with desired functionality, a single example being a device referred to herein as "medical device shaft" or a "working shaft," which can be used to securely or moveably support or house an injection shaft. For instance, an injection shaft can be incorporated permanently or movably (e.g., removably) against (alongside) or within (in a "working lumen" of) a working shaft. In exemplary embodiments an injection shaft can be loosely contained in a working lumen of a working shaft to allow movement of the injection shaft length-wise and rotationally relative to the working shaft; an injection shaft may be capable of moving longitudinally within a working lumen to allow the injection lumen to be extended distally from an open end of a working lumen at a distal end of the working shaft.

An example of a "working shaft" or "medical device shaft" can be a shaft that is useful in conjunction with an injection shaft, to manipulate and place the injection orifice of an injection shaft at a desired location for treatment of tissue. A "working shaft" or "medical device shaft" can function to support the injection shaft, and can optionally and preferably include any of a variety of optional functionalities such as steerability, an optical function, a tissue tensioner, or combinations of these, in addition to supporting the injection shaft.

An example of a particularly preferred working shaft can include features of a typical cystoscope, endoscope, ureteroscope, choledoscope, hysteroscope, catheter (e.g., urinary catheter), or the like, or other similar type of medical device shaft, including one or more feature of flexibility, an optical function, a steerable distal shaft end, and a working lumen. The working lumen can be sized to loosely house or contain the injection shaft, preferably in a manner to allow the injection shaft to be moved lengthwise and rotationally within the working lumen, relative to the working lumen, such as to allow the injection lumen to be extended from an opening of the working shaft at a distal end of the working shaft. A typical diameter (or other dimension) of a working lumen, extending along a length of a distal end of a working shaft, can be in the range from about 1 to about 3 millimeters. A typical length of working shaft for placement of a distal end at a location of the urinary tract can be, e.g., from 15 to 25 centimeters.

As used herein, the term "flexible shaft" refers to a shaft (e.g., an injection shaft or a working shaft) that is sufficiently pliable to allow bending and flexing that allow the shaft to be inserted through the meatus or an external incision, into the urethra or another body lumen, and to allow a portion of a distal end of the shaft to be guided into a body lumen such as a urethra and optionally the bladder neck or bladder, as can be done with a Foley catheter. A flexible shaft can be sufficiently soft and pliable to conform or partially conform to a patient's anatomy, such as would a Foley-type catheter. A "steerable" shaft is a type of a flexible shaft having a distal end that can be maneuvered directionally (e.g., bent or curved) from a proximal end; steerable shaft distal ends are sometimes features of endoscopes and other medical device shafts.

Optionally, a shaft of a device as described may also be malleable, or "shapeable," meaning that a shaft distal end, or portion thereof, can be of a material capable of being shaped to a form, and to remain in that form during use, such as for insertion into a body lumen, until re-formed. A shaft or a shaft component, such as a working shaft or an injection shaft, can include a malleable component such as a bendable metal wire, coil, ribbon, tube, or the like, capable of being shaped, used without substantial deformation, and re-shaped. A malleable distal end can allow a distal end to be shaped by a user to assist in placement of the distal end through a body lumen such as a urinary tract, at a desired location. In some methods of treatment, there may be difficulties or challenges in passing a shaft distal end through a body lumen, or to place the distal end in contact with tissue for injection. A malleable shaft distal end, e.g., of an injection shaft in particular, e.g., used in conjunction with a working shaft within which the malleable injection shaft distal end is moveably disposed, may assist in overcoming such potential difficulties. The malleable distal end tip may be formed by a user to a desired curve or bend, before or after placement in a working channel; the working shaft may be inserted into a body lumen such as a urethra, and the formed, malleably injection shaft distal end may be extended from the working shaft with a shape that improves the ability to position the injection shaft or ejection orifices thereof, at tissue for injection. A shapeable portion may vary in stiffness, length, resilience, material, radiopacity, etc., and may be of any malleable material such as a polymer, metal, or polymer-metal composite.

FIG. 9 illustrates an example of a malleable distal end. Shaft distal end 70 (e.g., injector shaft distal end) of FIG. 9 includes sidewall 72, injection orifice 76 and control orifice 80, directed in opposing directions, distal end tip 60, and cylindrical tissue holding tip proximal to distal end tip 60. Control orifice 80 is connected to control lumen 84, which communicates with a proximal end of a needleless injection device. Injection orifice 76 is connected to injection lumen 74, which communicates with a proximal end of a needleless injection device. Within sidewall 72 is malleable elongate member 75, which can be a metal, polymer, or metal-polymer composite, as described.

A distal end of a shaft (e.g., an injection shaft or a working shaft) includes one or multiple ejection orifices for ejecting fluid within a body of a patient, including at least one injection orifice. An ejection orifice may be for injecting fluid into tissue, in which case the ejection orifice is referred to as an "injection orifice"; alternate ejection orifices may be for ejection of non-therapeutic fluids, such as ejection of control fluid, in which case the ejection orifice may be referred to as a "control orifice." An injection orifice or a control orifice can be any form of opening, aperture, or orifice, such as an aperture or bore in an injection shaft sidewall or other shaft sidewall, or an aperture or bore in a nozzle, end effector, injection head, or other structure in communication with an injection lumen or control lumen, as desired.

Embodiments of devices as described can include multiple ejection orifices at a distal end. The orifices can be located at relative locations and orientations along a length or circumference of a shaft distal end to result in ejection and distribution of ejected fluid in different directions (e.g., circumferentially relative to the shaft), optionally or alternately at different distances along the length of the shaft. An ejection orifices can be directed at any angle relative to a longitudinal axis of a shaft, such as perpendicular, angled toward a distal end, or angled toward a proximal end.

An injection orifice may have any useful size (e.g., length and diameter) to produce a fluid stream of ejected fluid that can penetrate a tissue surface to become injected into tissue. Examples of a useful range of diameter of an injection orifice may be from about 0.001 to 0.05 inches, e.g., from 0.001 to 0.010 inches, depending on factors such as desired injection parameters (injection depth, volume, pressure, exit velocity, etc.) and the type and size (e.g., depth) of tissue being injected. An injection orifice may be larger or smaller than an injection lumen leading to the injection orifice, if desired, to affect the exit velocity of the jet of injectate from the injection orifice. Examples of useful orifice shapes may include features such as a venturi, a continuous uniform diameter along the length of an orifice, a funnel-shape, etc. These dimension and shape features can also apply to control orifice.

Ejection orifices, as indicated, can be of various structures and designs, such as a simple bore in a shaft, or a bore or aperture of a connected structure such as a nozzle, end effector, injection head, or other structure that can be connected to a shaft to allow communication between a lumen within the shaft, and an ejection orifice. Examples of alternate forms of ejection orifices are shown at FIGS. 8A, 8B, 8C, and 8D.

An example of one type of nozzle is show at FIGS. 8A and 8B. Referring to FIG. 8A, shaft distal end 50, an injection shaft, in cross-section, includes shaft sidewall 52, injection lumen 54, and is attached to and in fluid communication with nozzle 61. Nozzle 61 includes multiple injection orifices 56, directed (as illustrated), parallel with longitudinal axis $A_L$. Distal end tip 60 is coextensive with a surface 63 of nozzle 61, orthogonal to longitudinal axis $A_L$; in this embodiment, injection orifices 56 are at the same length-wise location as distal end tip 60 (the farthest most location of the distal end, which includes structure of nozzle 61).

The nozzle of FIGS. 8A (cross-sectional side view) and 8B (end vies) may be referred to as a "shower-head" nozzle, and can deliver various injectates (e.g., drugs) to a tissue surface, such as a surface of a shallow tissue, e.g., bladder tissue, through a multi-orifice, end-firing device shaft. Alternately, the nozzle may be useful for deep injections of other tissues. The shower-head nozzle is an attachment to shaft sidewall 52, secured and in communication communicate with single injection lumen 54 (alternately, multiple lumens), and includes multiple injection orifices placed at a surface of the nozzle, resulting in ejection of fluid in a direction along the longitudinal axis of the nozzle.

This angle of ejection of the injection orifices of FIGS. 8A and 8B, i.e., the angle between the direction of the ejection orifices and the longitudinal axis of the nozzle, is shown to be zero, but may be any other angle, such as an angle directed at least partially away from the longitudinal axis. For example, nozzle 61 of FIGS. 8C (cross-sectional and 8D (end view) includes injection apertures 56 directed at approximately 90 degrees relative to longitudinal axis $A_L$ of nozzle 61. Nozzle 61 of FIGS. 8C and 8D includes multiple injection orifices placed at a circumference of the nozzle, resulting in balanced ejection forces and distribution of injectate in a circumferential pattern, allowing for good dose distribution. The angle between the ejection orifices and the longitudinal axis is shown to be perpendicular, but may be angled more toward tissue, or away from tissue, as desired. As illustrated, nozzle 61 includes multiple frictional spikes 65, for engaging a tissue surface when nozzle 61 is place normally against a tissue surface; spikes 65 assist in preventing movement of nozzle 61 during an injection.

The control fluid may be supplied by a lumen or may be taken from the local environment of the of the catheter (irrigation fluid, urine, blood, etc.). A structure that defines the fluid stream of control fluid can be a control orifice, and may be in the form of an aperture or bore located in a sidewall of an injection shaft, or other structure such as a separate nozzle, vane, end effector, etc., that is placed at the shaft distal end.

Figure 10:
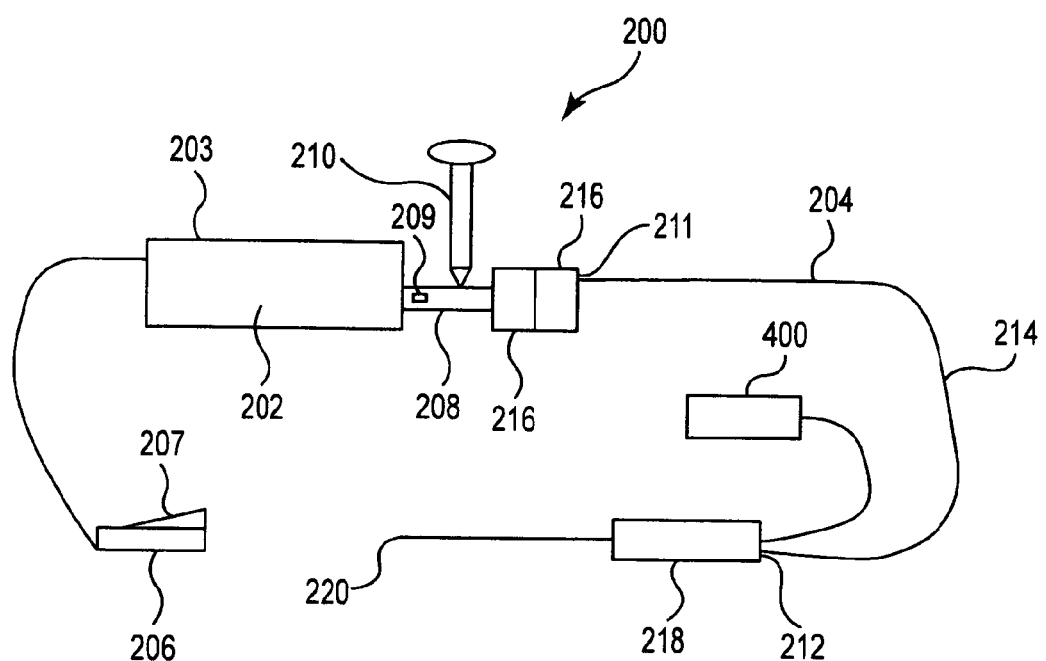
FIG. 10 is a schematic of an injector system incorporating the present invention.

A needleless fluid delivery system 200 is illustrated generally in FIG. 10. Needleless fluid delivery system 200 can comprise console (injector) 202 and shaft (applicator lumen) 204. Console 202 can be as simple as a manually activated syringe, or console 202 can comprise an automated console 203 including a user interface 206 and a connector member (e.g., in the form of a detachable pressure chamber) 208. Connector member 208 can include a surface opening 209 and a therapeutic fluid supply 210. User interface 206 can comprise an input means for selectively delivering a pressurized fluid through shaft 208. Representative input means can include foot pedal 207, switches, buttons or a touch-screen capable of receiving touch commands as well as displaying system information including a mode of operation as well as operating parameters.

As seen in FIG. 10, shaft 204 generally attaches to connector member 208. Shaft 204 is generally continuously defined from a (proximal) supply end 211 to a (distal) delivery end 212. Shaft 204 can comprise a variety of configurations including, for example, an endoscope or catheter configuration. In some embodiments, shaft 204 can comprise a flexible tube 214 to allow for easy positioning of the delivery end 212. Supply end 211 is generally configured to attach to the connector member 208 and can include a quick-connect style connector 216. Delivery end 212 can comprise a variety of configurations depending upon the style of the shaft 204 and a specified treatment location in a patient's body such as, for example, a rectal treatment location, a gastrointestinal treatment location, a nasal treatment location, a bronchial treatment location, or an esophageal treatment location. Various distal end configurations, such as end-fire and side-fire configurations, either with or without resultant balanced injection forces or control forces on a shaft 204, are useful.

In some embodiments, shaft 204 can include an application specific applicator 218 having a fluid administration port 220 (control orifice). A jet system 400, providing a fluid source (control fluid) and control system, can be connected to the applicator 218. It is envisioned that the jet system 400 includes an independent source of jet (control) fluid and an independent driving force such as a pressurized tank, magneto-hydrodynamic power, expanding steam, gas power or similar methods of propulsion. It is also envisioned that the jet system 400 can be incorporated into the injector 202.

Figure 11:
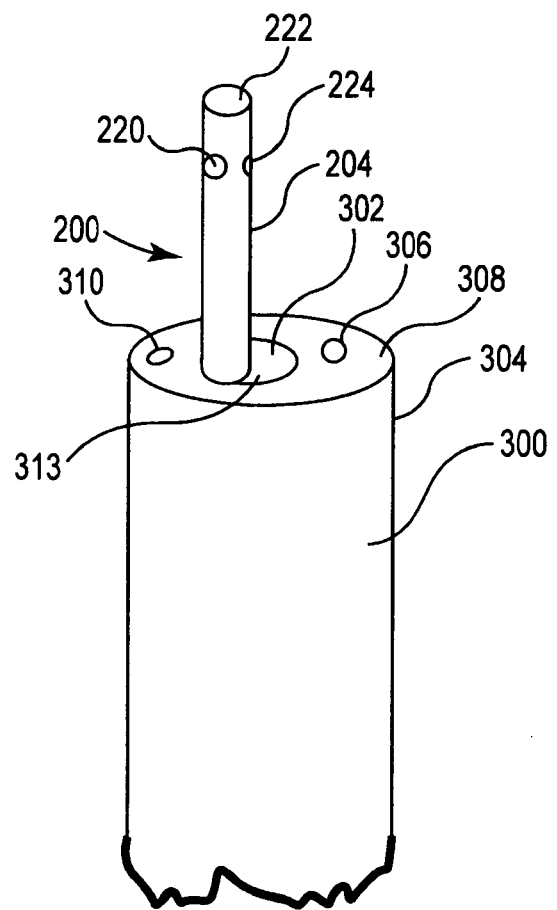
FIG. 11 is a perspective view of an exemplary access device and injector source.

As seen in FIG. 11 the shaft 204 of the needleless fluid delivery system 200 is inserted into the working channel 302 of a flexible endoscope or cystoscope 300. Applicator lumen (shaft) or injection lumen (injection shaft) 204 has a distal treatment end 222 proximate with a fluid administration port (injection orifice) 220 is disposed and at least one jet port (control orifice) 224 is disposed on an opposing side. The fluid administration port (injection orifice) 220 is fluidly connected to the injection source. The jet port (control orifice) 224 is fluidly connected to a jet fluid source or to the injection source.

Generally, flexible cystoscope 300 can comprise a length of polymeric tubing 304 having a distal treatment end 308. In some embodiments, flexible cystoscope 300 can deliver a therapeutic fluid to the treatment location through the polymeric tubing 304 or alternatively, the polymeric tubing can be use to provide access for medical instruments and/or tools such as, for example, a fiber optic scope and/or light to assist in diagnosing and/or treating tissue.

In positioning the flexible cystoscope 300 at a treatment location, it will be understood that a medical professional frequently employs a medical imaging system such as, for example, computer axial tomography (CAT), magnetic resonance imaging (MRI), or in the case of treatment of a prostate gland, the preferred imaging means is transrectal ultrasound (TRUS) so as to achieve the desired position of the distal treatment end 308. Through the use of a medical imaging system, or an optical component of a working shaft, a medical professional can verify that the distal treatment end 308 is properly positioned for delivering therapy at the treatment location.

Referring to FIG. 10, a flexible cystoscope 300 of the present invention can comprise a length of polymeric tubing 304 having a working channel (working lumen) 302 and one or more treatment tools such as, for example, fiber optic lights 306 and an objective lens 310. Located within working channel (working lumen) 302 can be one or more components of an injection device 200 that can include one or more injection shaft 204. Injection device 200 is configured so as to have a cross-sectional profile that does not fully occupy the working channel (working lumen) 302 so as to define an open channel 313. Injection device 200 simultaneously contacts the polymeric tubing 304 at a plurality of contact locations so as to maintain a desired orientation within the working channel 302 and to provide lateral support to the flexible cystoscope 300.

Polymeric tubing 204 and injection device 200 are preferably fabricated of medical grade polymers and copolymers. In some embodiments, polymeric tubing 204 and injection device 200 can be molded of the same polymer so as to promote maximum compatibility and similar performance characteristics. Depending upon the treatment application, polymeric tubing 204 and/or injection device 200 can be fabricated with high strength polymers including, for example, polyimide, polyetherimide available from General Electric under the trade name Ultem® and linear aromatic polymers such as PEEK™ available from Victrex plc. In some embodiments, the polymeric tubing 204 and/or the injection device 200 can be reinforced through the inclusion of materials including nano-particles, clays and/or glass within the polymer. Alternatively, polymeric tubing 204 and injection device 200 can be reinforced with one or more polymers such as, for example, tubes braided with Kevlar or other high-strength polymers. In some embodiments, the polymeric tubing 204 and/or injection device 200 can be fabricated so as to have a burst strength exceeding at least about 200 psi, e.g., 2,000 psi, and in some embodiments, having a burst strength within a range of about 2,000 psi to about 5,000 psi.

In use, flexible cystoscope 300 can be positioned for treatment as previously described with the cystoscope of the prior art. As the injection device 200 is slidably introduced into the working channel 302, the cross-section of the injection device 200 and more specifically, the injection lumen (injection shaft) 204, contacts locations that constrain the orientation and positioning of the injection lumen (injection shaft) 204 such that the injection lumen (injection shaft) 204 cannot buckle within the working channel 302. As the injection lumen (injection shaft) 204 cannot buckle within the working channel 302, open channel 313 remains unobstructed so as to accommodate irrigant flow to a treatment location. As injection lumen (injection shaft) 204 is advanced through the working channel 302, the injection lumen (injection shaft) 204 can be oriented such that the preferred axis of bending for the injection lumen (injection shaft) 204 matches the preferred axis of bending of the cystoscope 300 so as to resist twisting of the injection lumen (injection shaft) 204 and to maintain the desired orientation of the injection device 200.

Once the distal treatment end 308, and more specifically, the administration orifice or fluid injection port 220 is positioned with respect to the treatment location, the injector 200 can be actuated so as to begin delivery of a therapeutic fluid. If the fluid injection port 220 is not in contact with the treatment location, the jet system 400 can be activated to propel the injection lumen 204 toward the treatment location. As the jet fluid reaches distal treatment end 222, the jet fluid is rapidly accelerated through the jet orifice 224 to propel the lumen 204 toward the treatment area. Meanwhile, as the therapeutic fluid reaches distal treatment end 222, the therapeutic fluid is rapidly accelerated through the administration orifice (injection orifice) 220 to form a fluid jet that contacts the treatment area. Therapeutic fluid can be controllably dispensed directly at the treatment location so as to reduce the potential for exposure to other non-desired areas. The jet control system 400 should be able to compensate for the activation of the needless injection system 200.

Figure 12:
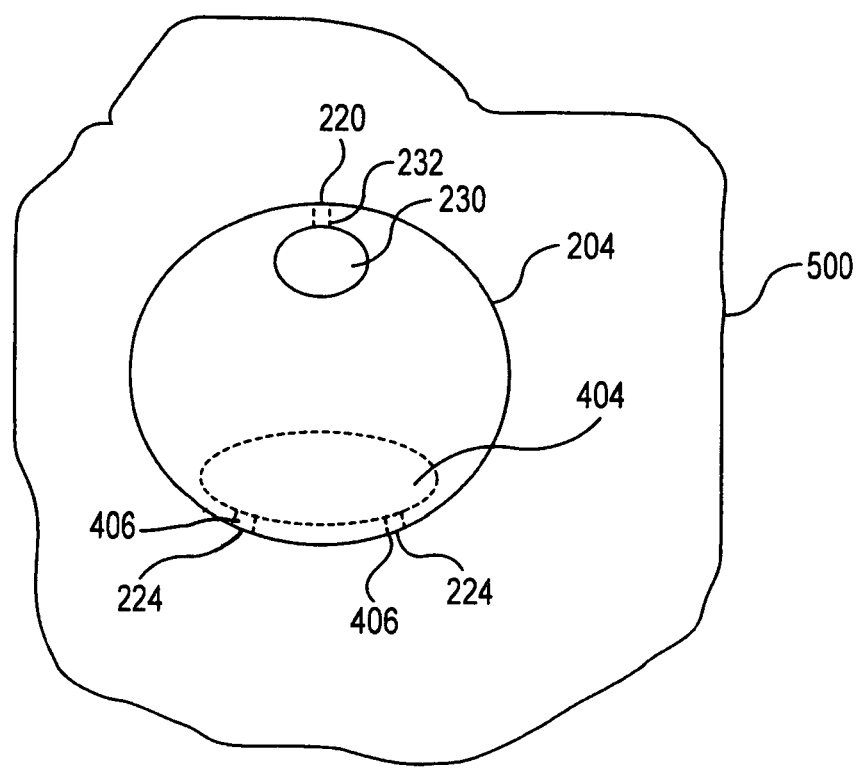
FIG. 12 is a cross sectional view of an exemplary injector source.

FIG. 12 illustrates the cross section of the injection lumen 204 proximate the jet ports (control orifice) 224 and injection port (injection orifice) 220 within a body cavity 500. An injection lumen 230 is fluidly connected to the injector 202. Therapeutic fluid is advanced through the injection lumen 230 to the injection nozzle 232 and out the injection port (injection orifice) 220. The jet ports (control orifices) 224 are each fluidly connected to a jet system 400 by way of apposition lumen (control lumen) 404. The jet or apposition fluid (control fluid) is advanced through the apposition lumen (control lumen) 404 to the apposition nozzles 406 and out the jet port (control orifice) 224.

Figure 13:
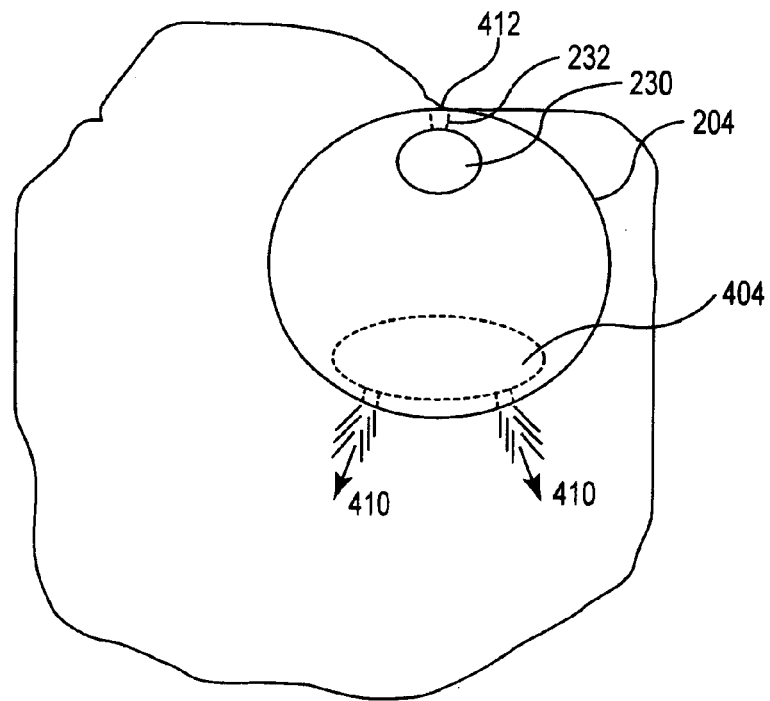
FIG. 13 is a cross sectional view of an exemplary injector source relative to a treatment location with jets firing.
Figure 14:
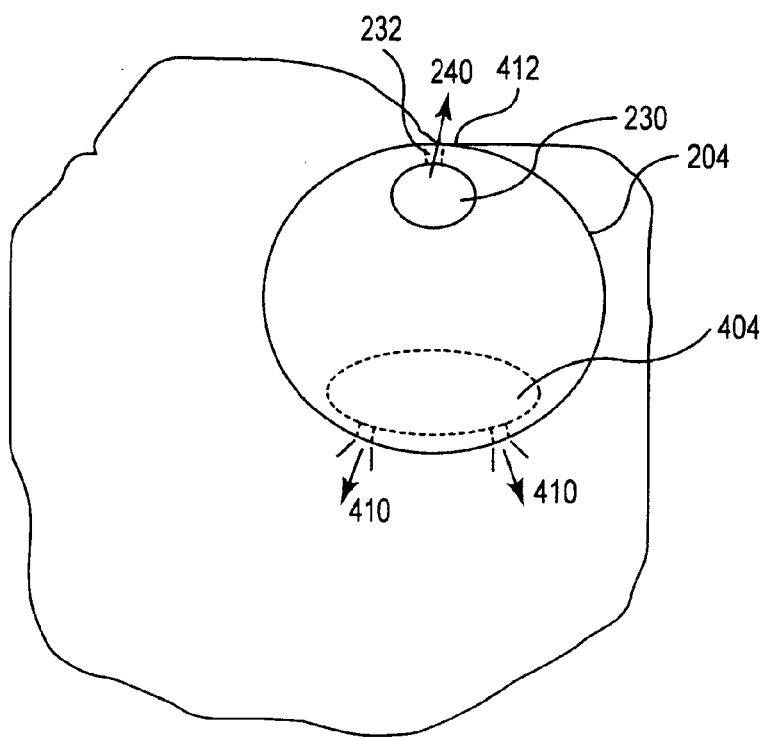
FIG. 14 is cross sectional view of an exemplary injector source relative to a treatment location with jet firing and the injector firing.

In operation, as illustrated in FIGS. 13 and 14, the jet system 400 is activated to create jets 410 (of control fluid) that direct lumen (injection shaft) 204 to the treatment location 412. While jets 410 continue firing, the therapeutic fluid advances through the injection lumen 230 to the injection nozzle 232. An injection jet 240 is then delivered to treatment area 412.

Figure 15:
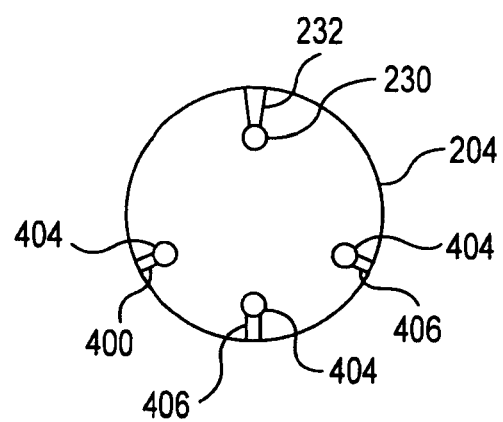
FIG. 15 is cross sectional view of an exemplary injector source.

It is envisioned that alternate embodiments, such as illustrated in FIG. 15, can be used for the jet system 400. For example, there can be multiple apposition lumens (control lumens) 404 each fluidly connected to a separate jetport 224. The apposition nozzles (control nozzle) 406 can be circular, crescent shaped, slits or any suitable shape. The apposition nozzles (control nozzles) can also be located circumferentially or axially about the lumen 204. While the above description makes repeated reference to a liquid jet, the system can operate by utilizing a compressed gas for the jets. It is further envisioned that an apposition lumen may not be necessary as the gas or liquid can be supplied from the catheter environment.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives.

Figure 16:
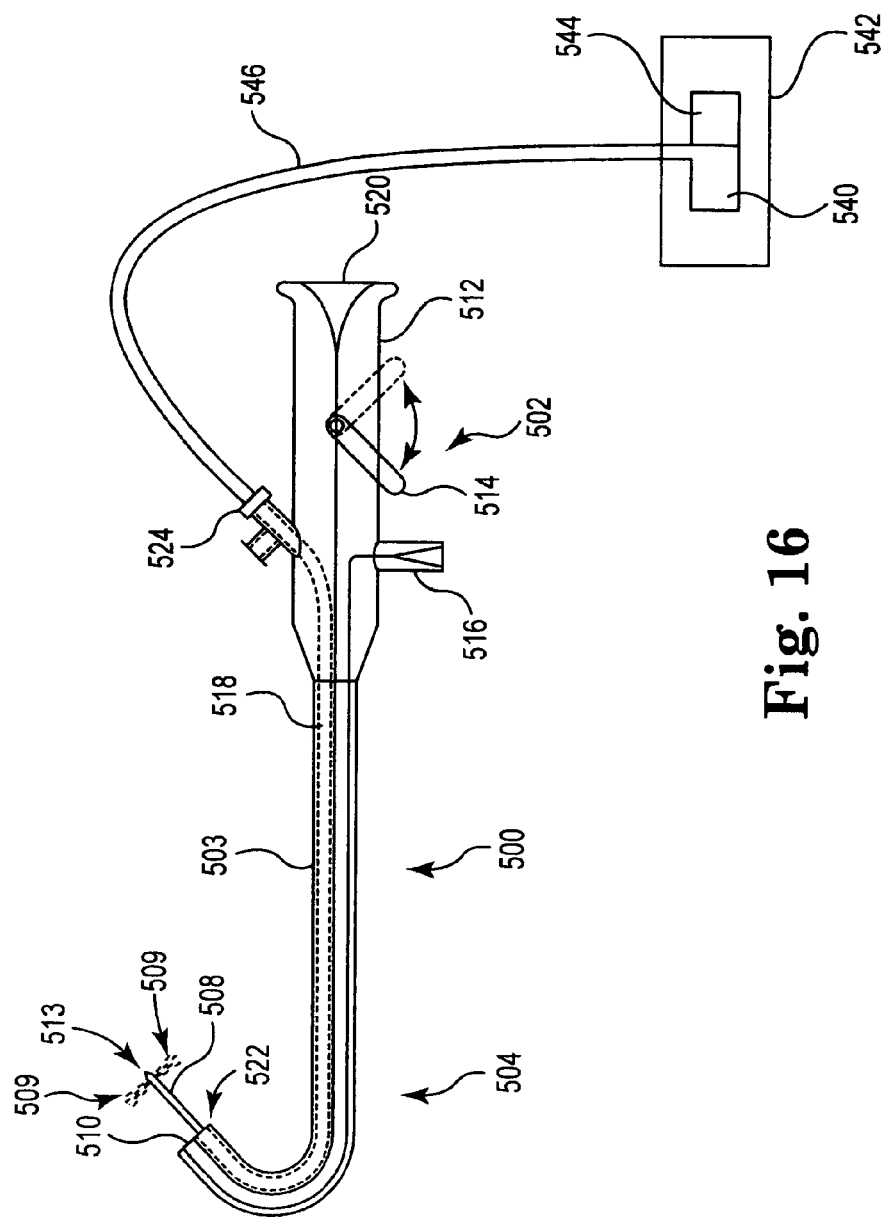
FIG. 16 illustrates a system as described.

Another exemplary embodiment of a needleless injection system according to the present description is illustrated at FIG. 16. Device 500 includes a handle 502 and working shaft distal end 504 of working shaft 503, which includes injection shaft 508 disposed within working lumen 518. The proximal end of the devices includes handle 502 of a scope that connects to working shaft 503 (e.g., of a cystoscope, endoscope, catheter, or other medical device shaft), including features useful for manipulating or operating features at distal end 504. Handle 502 includes: fiber optic light source 516; steering actuator 514, which can be manipulated to cause the steerable distal end of device 500 to move in at two or more dimensions); viewing lens 520 that allows viewing through fiber optic cable 510; and port 524, which allows for connection of a fluid source to handle 502. Articulation for steering of distal end 504 is indicated in dashed lines.

Still referring to FIG. 16, body 512 connects to working shaft 503, which includes lumens and mechanisms that connect features of proximal end handle 502 to distal end 504. Working lumen 518 is a hollow lumen or channel that extends within working shaft 503 and supports and contains injection shaft 508 in a manner that allows injection shaft 508 to move longitudinally along the length of working shaft 503, to allow the distal end of injection shaft 508 to extend from end opening 522 of working lumen 518. Working shaft 503 also includes fiber optic 510 and a steering mechanisms (not shown) that allows steering (deflecting) of distal end 504 by movement of actuator 514. Light source 516 transmits light to distal end 504 by fiber optic 510.

Distal end 504 includes end opening 522 of working lumen 518 from which can be extended injection shaft 508, which includes at least one injection orifice (not shown). Also distal end 504 can be steered to allow movement of the tip of working shaft distal end 504, in coordination with extension of injection shaft 508, based on viewing through fiber optic 510, to deliver a fluid with accurate placement at a desired tissue location. The distal end of injection shaft 508 can be any design as described herein, e.g., can include multiple ejection orifices at different length-wise or circumferential locations, optional control orifices, optional tissue holding tip, etc. As illustrated, fluid streams 509 are shown being ejected from injection orifice on opposite sides of the injection shaft distal end, on a proximal side of distal end tip 513 of injection shaft 508.

Also illustrated at FIG. 16 is shaft 546 extending between port 524 of handle 502 and console 542. Console 542 includes pressure chamber 540 and pressure source 544.

With any of the above features of fluid delivery devices, a device could include an electronic process control system that can be programmed to make fluid deliveries having various locations, volumes, and other injection properties such as depth and degree (e.g., shape and distance) of dispersion and size of particles of fluid.

A needleless injection system can be use to perform treatment methods by steps that include one or more of the following: providing a needleless injection device substantially as described herein; inserting a distal end of a shaft of the fluid delivery device into a patient, e.g., through the meatus and into the urethra; navigating the distal end until an injection orifice at the distal end of the shaft is positioned at a desired delivery site. Optionally depending on the type of treatment and tissue being treated the shaft distal end can be positioned in an orthogonal (normal) orientation relative to a tissue surface (optionally by assistance of a tissue holding tip and with pressure to cause bending of flexible injection shaft), such as if the tissue is bladder tissue; in these embodiments, longitudinal pressure may be placed on the distal end to cause a distal end tip to indent a tissue surface, optionally causing an injection orifice to become positioned at a level below a tissue surface, not by penetrating the surface but because the injection orifice is located at the indented tissue. In alternate methods a distal end can be positioned with a sidewall in contact with tissue, with a longitudinal axis of the shaft in line with (e.g., parallel to) tissue; a sidewall of the shaft distal end can be optionally be pressed against the tissue surface to cause an injection orifice to contact the tissue surface for injection, such as by the use of one or more control orifice to produce a control force.

By any of the described methods, multiple ejection orifices can provide the ability to place one or more different fluids at multiple locations of the urethra, prostate, bladder, or bladder neck, or other tissue, etc. Features of devices described herein, such as optical features, steerable shafts, extendable or moveable fluid delivery orifices, and the ability to deliver multiple different types of fluid, allow for improved control over the location of injection or instillation of a fluid.

Exemplary methods of treatment can include one or multiple discrete steps relating to insertion of a fluid delivery device as described herein; positioning of the device to place one or more fluid delivery orifices at desired locations within the bladder or bladder neck or other location of the urinary tract; optionally, use of an optic device; optional extension of a needle or a needleless delivery orifice extension from the shaft of the device to contact tissue of the bladder or bladder neck, etc.; delivery of one or more biologically active fluid or agent from a delivery orifice (needle or needleless delivery orifice) to either contact or penetrate tissue of the bladder or bladder neck, etc.; optionally, one or multiple steps of re-positioning one or more fluid delivery orifices; optionally, one or more additional delivery steps that involve the same or different delivery orifices.

According to fluid delivery procedures of the invention, fluid such as ethanol or a biologically active agent can be delivered to the bladder, urethra, urethra, or bladder neck, etc., in a manner that causes the fluid to be injected into the tissue using a needleless delivery orifice.

Devices of the present description can be useful to treat of various tissues, including of the urinary tract, in females or males. For example, devices as described may be useful to inject the bladder, bladder neck, the urethral tissue itself or the external sphincter, or for transurethral injection of the prostate in a male. Other treatment locations can include a rectal treatment location, a gastrointestinal treatment location, a nasal treatment location, a bronchial treatment location, and an esophageal treatment location. In other embodiments, a fluid may be injected into tissue of the urinary tract (e.g., bladder, urethra, kidneys, ureters, prostate, etc.) such as individual or combination treatments using drugs or other therapeutic agents, e.g., botulinum toxin ("botox"), an antiandrogen, among others as will be understood. One advantage of injection of an active pharmaceutical agent at a location of use is the placement of the agent to avoid systemic side effects. Specific examples of active pharmaceutical agents that may be injected include Botulinum toxin types A through G; 5-alpha reductase inhibitors such as dutasteride and finasteride; alpha blockers such as alfuzosin, doxazosin, prazosin, tamsulosin hydrochloride, terazosin, ethanol, to treat BPH; or any of various antibiotics (e.g., to treat prostatitis) and analgesics.

The invention also contemplates needleless injection systems that include any combination of components as described, including one or more console (e.g., a housing with one or more removable pressure chamber); one or more additional pressure chamber for dispensing one or a variety of different fluids to a single patient or to multiple patients; one or multiple different injection shaft attachments for dispensing the same or different fluids to one or multiple patients; and one or multiple working shaft. As an example, a combination of the invention may include multiple different injection shaft attachments, each having a proximal end that can be attached and removed from a console, e.g., a removable pressure chamber. Each injection shaft attachment can be the same or different, e.g., for treating bladder tissue (e.g., having an end-fire distal end, optionally balanced control orifices, optionally also a tissue holding tip), for treating prostate tissue (e.g., having a side-fire distal end, optionally one or more control orifice). One or multiple working shafts may also be suited to different treatments, e.g., one to treat prostate tissue, one to treat bladder tissue.

Figure 17:
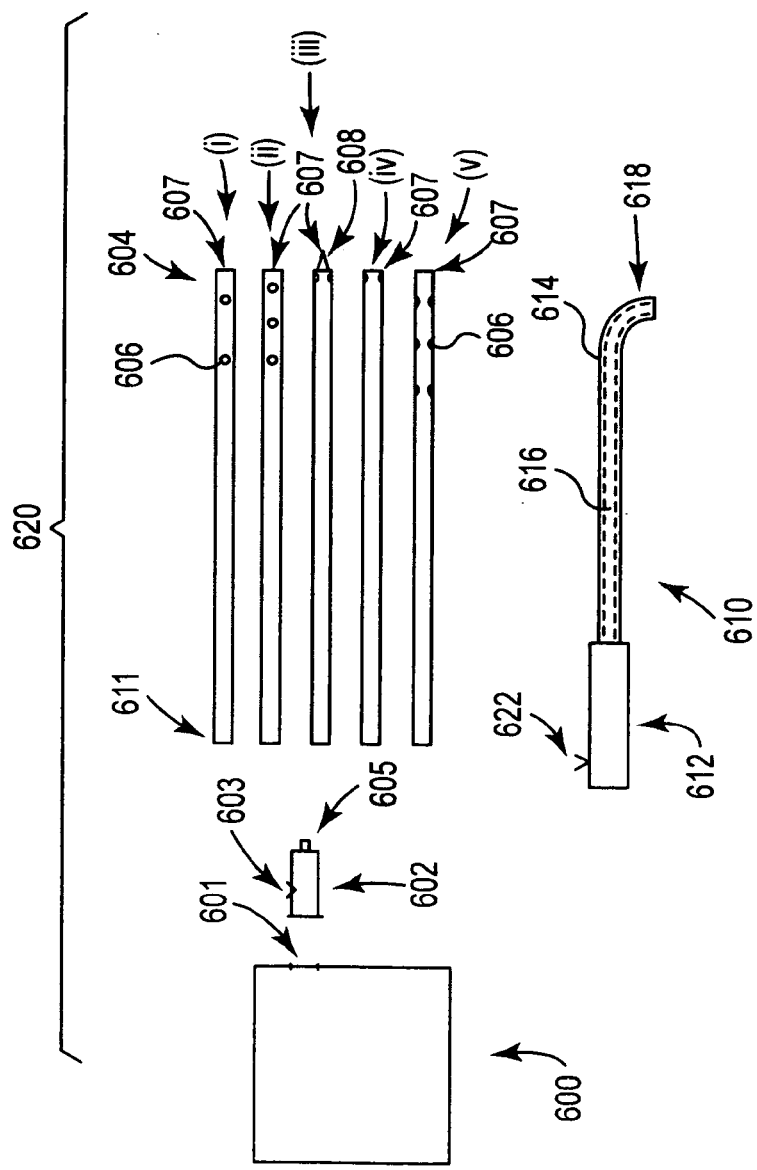
FIG. 17 illustrates options of combinations of systems as described.

FIG. 17 illustrates components of combination 620 of the invention Any different combination of components can be included in a system or set. The components include console 600, optional "connector member" or external, removable pressure chamber 602, multiple varieties of injection shaft attachments (i) through (v) that can be separately attached to console 600 or removable pressure chamber 602, and a single working shaft 610 including handle 612. Console or console housing 600 can be as described, and includes at least a pressure source. Port 601 allows connection to optional removable pressure chamber 602, which can be connect at a proximal end to port 601, and has distal end 605 that can be connected to a proximal end of an injection shaft attachment. Optional port 603 of pressure chamber 602 can be used to insert fluid into pressure chamber 602. Each of injection shaft attachments (i), (ii), (iii), (iv), and (v), are exemplary and for purposes of illustration of exemplary combinations. Each includes a proximal end (611) that can removably attach to console or console housing 600, optionally by removably attaching to connector member 602 at distal end 605. Each injection shaft attachment also includes one or more injection orifice 606 at a distal end 604, connected through an inflation lumen (not shown) to the proximal end. Each injection orifice as illustrated is on a proximal side of a distal end tip 607.

An optional component of combination 620 is working shaft 610, which may be as described herein, e.g., including handle 612, port 622 suitable to introduce an injection shaft into working lumen 616 of working shaft 614, optional steerable distal end 618, and an optional optical feature (not shown).

A combination can include any one or combination of injection shaft attachments as shown or otherwise described herein. An exemplary injection shaft attachment can include any one or more of a side-fire distal end with no control orifice (i), e.g., for deep injection treatment of prostate tissue; a side-fire distal end with a malleable distal end feature (not shown) (ii), e.g., for deep injection treatment of prostate tissue; an end-fire distal end with balanced injection orifices and a tissue holding tip (iii), e.g., for shallow injection treatment of bladder tissue; an end-fire distal end with balanced injection orifices and no tissue holding tip and optional control orifices (not shown) (iv), e.g., for shallow injection treatment of bladder tissue; or a side-fire distal end with multiple injection orifices along a length of a distal end and multiple opposed control orifices (v), e.g., for deep injection treatment of prostate tissue.

Other embodiments of this invention will be apparent to those of ordinary skill upon consideration of this description or from practice of the invention described and illustrated herein. Various omissions, modifications, and changes to the principles and embodiments described herein may be made by one skilled in the art without departing from the true scope and spirit of the invention which is indicated by the following exemplary embodiments of devices.

The invention claimed is:

1. A method of injecting tissue comprising
providing a needleless injection device comprising
a flexible shaft comprising a proximal end, a distal end, a distal end tip, and an injection lumen extending from the proximal end to the distal end,
the distal end comprising an injection orifice at a lengthwise location of the distal end on a proximal side of the distal end tip, the injection orifice in communication with the injection lumen, the injection orifice directed at an angle in the range from 45 to about 100 degrees relative to a longitudinal axis of the shaft at the length-wise location of the injection orifice,
wherein the shaft is capable of ejecting a fluid stream from the injection orifice, the fluid stream being capable of being injected into tissue by penetrating a tissue surface as a fluid stream at a non-normal angle relative to the tissue surface, and
an elongate tissue holding tip extending longitudinally from the distal end tip, the elongate tissue holding tip being capable of frictionally engaging tissue to prevent movement of the injection orifice during injection,
providing injectate at the proximal end and in communication with the injection lumen,
placing the injection orifice near a tissue surface without penetrating the tissue surface,
pressurizing the injectate to cause the injectate to be ejected from the injection orifice as a fluid stream that passes through the tissue surface and disperses as fluid particles in tissue below the tissue surface.

2. A method according to claim 1 wherein the shaft comprises a sidewall extending from the proximal end to the distal end and the injection orifice comprises an aperture passing through the sidewall.

3. A method according to claim 1 wherein
fluid ejected from the injection orifice produces an injection force on the distal end, and
the tissue holding tip comprises a pointed elongate extension capable of frictionally engaging tissue to prevent movement of the injection orifice during injection.

4. A method according to claim 3 wherein
fluid ejected from the injection orifice produces an injection force on the distal end, and
the distal end comprises a control orifice from which fluid can be ejected to produce a control force to oppose the injection force.

5. A method according to claim 3, wherein
the device comprises a working shaft comprising a working shaft proximal end, a working shaft distal end, and a working lumen extending between the working shaft proximal end and the working shaft distal end, and
the flexible shaft is contained in the working lumen in a manner that allows the flexible shaft to move longitudinally within the working lumen.

6. A method according to claim 5 wherein the working shaft comprises
a steerable distal end,
an end opening from which the flexible shaft distal end can be extended,
fiber optics, and
a light source.

7. A method according to claim 1 wherein the elongate tissue holding tip comprises an elongate shaft and a distal end pointed cone.

8. A method according to claim 1 wherein the elongate tissue holding tip has a longitudinal axis that is shared with or parallel to a longitudinal axis of the shaft.

9. A needleless method of injecting tissue, the method comprising
providing a needleless injection device comprising
a flexible shaft comprising a proximal end, a distal end, a distal end tip, and an injection lumen extending from the proximal end to the distal end,
an elongate tissue holding tip extending longitudinally from the distal end tip, the elongate tissue holding tip being capable of frictionally engaging tissue to resist movement of the injection orifice during injection,
the distal end comprising an injection orifice at a lengthwise location of the distal end on a proximal side of the distal end tip, the injection orifice in communication with the injection lumen, the injection orifice directed at an angle in the range from about 45 to about 100 degrees relative to a longitudinal axis of the shaft at the length-wise location of the injection orifice, positioning the distal end at a location to contact a tissue surface and normal to the tissue surface, with the elongate tissue holding tip depressing the tissue, and without the injection orifice penetrating the tissue surface, ejecting a fluid stream from the injection orifice such that the fluid stream penetrates the tissue surface at a non-normal angle relative to the tissue surface.

10. A method according to claim 9 comprising positioning the distal end tissue surface and normal to the tissue surface without the elongate tissue holding tip puncturing the tissue surface, and placing a normal pressure on the distal end to cause the distal end tip to indent the tissue surface.

11. A method according to claim 9 wherein ejection of fluid from the injection orifice produces an injection force on the distal end.

12. A method according to claim 11 comprising at least partially opposing the injection force.

13. A method according to claim 12 wherein the injection force is opposed by the tissue holding tip and one or more of: an opposing force produced by a control orifice, or an opposing force produced by an injection orifice.

14. A method according claim 9 comprising injecting bladder tissue.

* * * * *